US012171782B2

(12) United States Patent
Koch

(10) Patent No.: US 12,171,782 B2
(45) Date of Patent: Dec. 24, 2024

(54) FORMULATION, USE AND METHOD FOR BROAD-SPECTRUM PROPHYLAXIS AND TREATMENT OF VIRAL INFECTIONS CAUSED BY SARS-COV-2 AND OTHER EMERGENT VIRUSES

(71) Applicant: MELISA INSTITUTE, GENOMICS & PROTEOMICS RESEARCH S, Concepción (CL)

(72) Inventor: Elard Koch, Concepcion (CL)

(73) Assignee: MELISA INSTITUTE, GENOMICS & PROTEOMICS RESEARCH SpA, Concepción (CL)

( * ) Notice: Subject to any disclaimer, the term of this patent is extended or adjusted under 35 U.S.C. 154(b) by 0 days.

(21) Appl. No.: 18/388,618

(22) Filed: Nov. 10, 2023

(65) Prior Publication Data

US 2024/0148783 A1 May 9, 2024

Related U.S. Application Data

(62) Division of application No. 17/351,732, filed on Jun. 18, 2021, now abandoned.

(60) Provisional application No. 63/040,887, filed on Jun. 18, 2020.

(51) Int. Cl.
*A61K 33/30* (2006.01)
*A61K 47/54* (2017.01)
*A61P 31/14* (2006.01)

(52) U.S. Cl.
CPC ............ *A61K 33/30* (2013.01); *A61K 47/547* (2017.08); *A61P 31/14* (2018.01)

(58) Field of Classification Search
CPC ........ A61K 33/30; A61K 47/547; A61P 31/14
See application file for complete search history.

(56) References Cited

U.S. PATENT DOCUMENTS

| | | | |
|---|---|---|---|
| 7,405,046 B2 | 7/2008 | Rosenbloom | |
| 7,491,413 B2 | 2/2009 | Morré et al. | |
| 2011/0052727 A1 | 3/2011 | Polansky | |
| 2011/0257258 A1 | 10/2011 | Hensley et al. | |
| 2014/0088184 A1 | 3/2014 | Seron et al. | |

FOREIGN PATENT DOCUMENTS

| | | |
|---|---|---|
| CN | 105687226 A | 6/2016 |
| EP | 1655292 B1 | 4/2015 |
| JP | 2004135462 A | 4/2004 |
| JP | 2006100710 A1 | 8/2008 |
| JP | 2018024610 A1 | 2/2018 |
| TW | 200533342 A | 10/2005 |

OTHER PUBLICATIONS

Alhafez et al., "Synthesis, characterization and antioxidant activity of EGCG complexes with copper and zinc ions", Journal of Coordination Chemistry, 2019, pp. 1-15.

Baéz-Santos et al., "The SARS-coronavirus papain-like protease: Structure, function and inhibition by designed antiviral compounds", Antiviral Research, vol. 115, 2015, pp. 21-38.

Bozym et al., "Measuring Picomolar Intracellular Exchangeable Zinc in PC-12 Cells Using a Ratiometric Fluorescence Biosensor", ACS Chemical Biology, vol. 1, No. 2, 2006, pp. 103-111.

Callaway et al., "Coronavirus by the Numbers", Nature, vol. 579, Mar. 2020, pp. 482-483.

Chauteverdi et al., "Viral infections and trace elements: A complex interaction", Current Science, vol. 87, No. 11, Dec. 2004, pp. 1536-1554.

Clergeaud et al., "A simple liposome assay for the screening of zinc ionophore activity of polyphenols", food Chemistry, vol. 197, 2016, pp. 916-923.

Colvin et al., "Insights into Zn2+ homeostasis in neurons from experimental and modeling studies", Am J. Physiol Cell Physiol., vol. 294, 2008, pp. C726-C742.

Dabbagh-Bazarbachi et al., "Zinc lonophore Activity of Quercetin and Epigallocatechin-gallate: From Hepa 1-6 Cells to a Liposome Model", American Chemical Society, vol. 62, 2014, pp. 8085-8093.

De Oliveira et al., "Inhibition of Herpes Simplex Virus type 1 with the modified green tea polyphenol palmotoyl-epigallocatechin gallate", Food Chem Toxicol. vol. 52, Feb. 2013, pp. 207-215.

Eby et al., "Reductional in Duration of Common Colds by Zinc Gluconate Lozenges in a Double-Blind Study", Antimicrobial Agents and Chemotherapy, vol. 25, No. 1, Jan. 1985, pp. 20-24.

Feng et al., "Rational use of Face Masks in the COVID-19 pandemic", Elsevier, www.thelancet.com/respiratory, vol. 8, May 2020, pp. 1, 434-436.

Furuta et al., "Concise synthesis of dideoxy-epigallocatechin gallate (DO-EGCG) and evaluation of its anti-influenza virus activity", Bioorganic & Medicinal chemistry Letters, vol. 17, 2007, pp. 3095-3098.

Han et al., "Papain-Like Protease 2 (PLP@) from Severe Acute Respiratory Syndrome Coronavirus (SARS-CoV): Expression, Purification, Characterization, and Inhibition", Biochemistry, vol. 44, 2005, pp. 10349-10359.

(Continued)

*Primary Examiner* — Timothy R Rozof

(74) *Attorney, Agent, or Firm* — Norris McLaughlin, P.A.

(57) ABSTRACT

EGCG-$Zn^{2+}$ molecular complexes exhibit a significantly higher affinity than the EGCG molecule alone or $Zn^{2+}$ alone for binding to different SARS-CoV-2 molecular targets and show virtually complete antiviral suppressive activity (>99%) against this virus in experimental models of infection. EGCG-$Zn^{2+}$ complexes have a lower toxicity than EGCG alone in transfected human cells. The combination of EGCG and $Zn^{2+}$, significantly improved some key pharmacokinetic parameters of EGCG in humans. Thus, these complexes can be used as a new broad-spectrum method for chemoprophylaxis or treatment of viral diseases by using formulations containing a composition of EGCG and $Zn^{2+}$ or EGCG-$Zn^{2+}$ complexes in sufficient amount to reach a blood concentration with antiviral effect, minimizing safety issues in humans.

30 Claims, 11 Drawing Sheets

(56) References Cited

OTHER PUBLICATIONS

Henss et al., "The green tea catechin epigallocatechin gallate inhibits SARS-CoV-2 infection", Journal of General Virology, vol. 102, Apr. 2021, pp. 1-8.
Hong et al., "Epigallocatechin Gallate Inhibits the Uridylate-Specific Endoribonuclease Nsp15 and Efficiently Neutralizes the SARS-Cov-2 Strain", J. Agric. Food. Chem. vol. 69, No. 21, Jun. 2021, pp. 5948-5954.
Hsu et al., "Evaluation of metal-conjugated compounds as inhibitors of 3CL protease of Sars-Cov", FEBS Letters, vol. 54, 2004, pp. 116-120.
Huang et al., (−)-Epigallocatechin-3-gallate inhibits entry of hepatitis B virus into hepatocytes, Antiviral Research, ScienceDirect, Elsevier, Sep. 2014, pp. 1-12.
Hurst et al., "Epigallocatechin-3-Gallate (EGCG) Inhibits SARS-CoV-2 Infection in Primate Epithelial Cells", Microbiol Infect Dis., vol. 5. No. 2, Apr. 2021, pp. 1-6.
Isaacs et al., "Epigallocatechin Gallate Inactivates Clinical Isolates of Herpes Simplex Virus", Antimicrobial Agents and Chemotherapy, vol. 52, No. 3, Mar. 2008, pp. 962-970.
Ishii et al., Covalent modification of proteins by green tea polyphenol (−)-epigallocatechin-3-gallate through autoxidation, Free Radical Biology & Medicine, vol. 45, 2008, pp. 1384-1394.
Kaihatsu et al., "Antiviral Mechanism of Action of Epigallocatechin-3-O-gallate and Its Fatty Acid Esters", Molecules, vol. 23, 2018, pp. 1-21.
Kopecky-Bromberg et al., "Severe Acute Respiratory Syndrome Coronavirus Open Reading Frame (ORF) 3b, ORF 6, and Nucleocapsid Proteins Function as Interferon Antagonists", Journal of Virology, Jan. 2007, pp. 548-557.
Krenn et al., "Antiviral Activity of the Zinc lonophores Pyrithione and Hinokitiol against Picornavirus Infections", Journal of Virology, vol. 83, No. 1, Jan. 2009 pp. 58-64.
Ling et al., "Amelioration of influenza virus-induced reactive oxygen species formation by epigallocatechin gallate derived from green tea", Acta Pharmacologica Sinica, vol. 33, 2012, pp. 153-1541.
Lotfinejad et al., "Hand hygiene and novel coronavirus pandemic: the of healthcare workers". Elsevier, Journal of Hospital Infection, vol. 105, 2020, pp. 1, 776-777.
Matsumoto et al., "Inhibitory effects of epigallocatechin gallate on the propagation of bovine coronavirus in Madin-Darby bovine kidney cells", Animal Science, vol. 76, 2005, pp. 507-512.
Maxfield et al., "Zinc Deficiency", http://www.ncbi.nlm.nih.gov/books/NBK493231/?report, 2019, pp. 1-10.
Nakayama et al., "Inhibition of the infectivity of influenza virus by tea polyphenols", Antiviral Research, vol. 21, 1993, pp. 289-299.
Nguyen et al., "Flavonoid-mediated inhibition of SARS coronavirus 3C-like protease expressed in Pichia pastoris", Biotechnol Lett, vol. 34, 2012, pp. 831-838.
Niemeyer et al., "The papain-like protease determines a virulence trait that varies among members of the SARS-coronavirus species", PLOS Pathogens, http://doi.org/10.1371/journal.ppat.10007296, Sep. 2018, pp. 1-27.
Prasad, "Zinc: role in immunity, oxidative stress and chronic inflammation", Current Opinion in Clinical Nutrition Metabolic Care, vol. 12, 2009, pp. 646-652.
Quesada et al., "Dietary catechins and procyanidins modulate zinc homeostasis in human HepG2 cells", Journal of Nutritional Biochemistry, vol. 22, 2011, pp. 153-163.
Roh, "A facile inhibitor screening of SARS coronavirus N protein using nanoparticle-based RNA oligonucleotide", Int'l Journal of Nanomedicine, vol. 7, 2012, pp. 2173-2179.
Samutprasert et al., "Epigallocatechin gallate-zinc oxide co-crystalline nanoparticles as an inticancer drug that is nontoxic to normal cells", RSC Advances, vol. 8, 2018, pp. 7369-7376.
Shiha et al., "Addition of Epigallocatechin Gallate 400 mg to Sofosbuvir 400 mg + Daclatisvir 60 mg With or Without Ribavirin in Treatment of Patients with Chronic Hepatitis C Improves the Safety Profile: A Pilot Study", Scientific Reports, vol. 9, 2019, pp. 1-8.
Skalny et al., Zinc and respiratory tract infections: Perspectives for COVID-19 (Review), Int'l Journal of Molecular Medicine, vol. 46, 2020, pp. 17-26.
Steinmann et al., "Anti-infective properties of epigallocatechin-3-gallate (EGCG), a component of green tea", British Journal of Pharmacology, vol. 168, 2013, pp. 1059-1073.
Suara et al., "Effect of Zinc Salts on Respiratory Syncytial Virus Replication", Antimocrobial Agents and Chemotherapy, vol. 48, No. 3, Mar. 2004, pp. 783-790.
Sun et al., "Free Zn2+ enhances inhibitory effects of EGCG on the growth of PC-3 cells", Mol. Nutr. Food Res., vol. 52, 2008, pp. 465-471.
Surjit et al., "The SARS-CoV nucleocapsid protein A protein with multifarious activities", Infection, Genetics and Evolution, vol. 8, 2008, pp. 397-405.
Thambiayya et al., "Functional role of intracellular labile zinc in pulmonary endothelium", Pulmonary Circulation, vol. 2, No. 4, Oct.-Dec. 2012, pp. 443-451.
Uchide et al., "Effect of antioxidants on apoptosis induced by influenza virus infection: inhibition of viral gene replication and transcription with pyrrolidine dithiocarbamate", Antiviral Research, vol. 56, 2002, pp. 207-217.
Vabret et al., "Immunology of COVID-19 Current State of the Science", Immunity, vol. 52, Jun. 2020, pp. 910-941.
Velthuis et al., "Zn2+ Inhibits Coronavirus and Arterivirus RNA Polymerase Activity in Vitro and Zinc Ionophores Block the Replication of These Viruses in Cell Culture", PLos Pathogens, www.plospathogens.org, vol. 6, No. 11, Nov. 2010, pp. 1-10.
Wu et al., "Analysis of therapeutic targets for SARS-CoV-2 and discovery of potential drugs by computational methods", Acta Pharmaceutica Sinica B, vol. 10, No. 5, Feb. 2020, pp. 766-788.
Xu et al., "A Review of the Antiviral Role of Green Tea Catechins", Molecules, No. 22, 2017, pp. 1-18.
Yang et al., "Epigallocatechin-3-gallate affects the growth of LNCaP cells via membrane fluidity and distribution of cellular zinc", J. Zhejiang Univ. Sci. B, vol. 10, No. 6, 2009, pp. 411-421.
Yen et al, "Interrupting COVID-19 transmission by Implementing enhanced traffic control budling: Implications for global prevention and control efforts", Journal of Microbiology, Immunology and Infection, vol. 53, 2020, pp. 377-380.
Zhang et al., "Preparation, characterization and evaluation of tea polyphenol-Zn complex loaded B-chitosan nanoparticles", Food Hydrocolloids, 2015, pp. 1-57.
Zhang et al., "Crystal structure of SARS-VoV-2 main protease provides a basis for design of improved a-ketoamide inhibitors", Science, vol. 368, Apr. 2020, pp. 409-412.
Zhong et al., "Epigallocatechin-3-gallate opposes HBV-induces incomplete autophagy by enhancing lysosomal acidification, which is unfavorable of HBV replication", Cell Death and Disease, vol. 6, 2015, pp. 1-9.

FORMULATION, USE AND METHOD FOR BROAD-SPECTRUM PROPHYLAXIS AND TREATMENT OF VIRAL INFECTIONS CAUSED BY SARS-COV-2 AND OTHER EMERGENT VIRUSES

FIELD OF THE INVENTION

The present invention relates to a broad-spectrum antiviral formulation and method for the pre- and post-exposure prophylaxis and treatment of viral infections with very low toxicity in humans; more particularly, to a formulation and method for the pre- and post-exposure prophylaxis and treatment of an infection caused by emerging enveloped viruses such as SARS-CoV-2.

SUMMARY OF THE INVENTION

The present invention provides a method of treatment for an individual; the use of a formulation; and a formulation that has been developed and created taking into consideration the extraordinary ability of epigallocatechin-3-gallato (herein EGCG) to bind $Zn^2$ ions by chelation, spontaneously and efficiently forming coordinated covalent molecular compounds of EGCG-$Zn^{2+}$ (herein EGCG-$Zn^{2+}$ complexes) at physiological pH 7.4. The inventors have found that these EGCG-$Zn^{2+}$ complexes have a significantly higher affinity than the EGCG molecule alone or than $Zn^{2+}$ alone for binding to different SARS-CoV-2 molecular targets and show virtually complete antiviral suppressive activity (>99%) against this virus in experimental models of infection. The inventors have experimentally confirmed that EGCG-$Zn^{2+}$ complexes present lower toxicity than EGCG alone in transfected human cells. In addition, the inventors found that the combination of EGCG and $Zn^{2+}$, significantly improved some key pharmacokinetic parameters of EGCG in humans. Therefore, these complexes can be used as a new broad-spectrum method for chemoprophylaxis or treatment of viral diseases by using formulations containing a composition of EGCG and $Zn^{2+}$ or EGCG-$Zn^{2+}$ complexes in sufficient amount to reach a blood concentration with antiviral effect, minimizing safety issues in humans.

BACKGROUND OF THE INVENTION

Emerging virus infections continue posing significant public health issues and challenges with the potential to cause epidemics and pandemics. The most recent outbreak is the SARS-CoV-2 (viral agent for COVID-19), which rapidly reached catastrophic levels in several countries (Callaway et al 2020). Although vaccines are one of the most effective measures for infectious disease prophylaxis, unfortunately they are not immediately available to stop a new pathogen. To reduce or slow the morbidity and mortality of a new virus, a variety of prophylactic public health interventions are implemented including face masks, hand hygiene, social distancing, decreased circulation, quarantines, isolation, traffic control, etc. (Feng et al 2020; Lotfinejad et al 2020; and Yen et al 2020) Unfortunately, these latest public health interventions are insufficient and often outmatched when the emerging virus has already reached pandemic proportions. Consequently, there is an urgent need to develop broad-spectrum antiviral chemoprophylactic and therapeutic drugs for use in humans, while minimizing safety concerns.

Epigallocatechin-3-Gallate as Antiviral Agent

Epigallocatechin-3-gallate (EGCG) is a catechin extracted and purified from *Camellia sinensis* (green tea) that is promising and well known as a potential intervention to prevent infection through many types of viruses (Xu et al 2017; Steinmann et al 2013). Multiple lines of experimental evidence have confirmed EGCG has a potent antiviral activity with different modes of action, and in various families of viruses, such as Retroviridae, Orthomyxoviridae, and Flaviviridae. It includes important human pathogens, such as influenza virus, rhinovirus, hepatitis B (HBV) and C (HCV) virus (see for example patents by Seron et al 2014; Hensley et al 2011; Moue et al 2009; Polansky et al 2011; and Rosenbloom 2008). EGCG exerts a powerful inhibition of influenza viral RNA replication, interferes with HBV/HCV entry and inactivates simple herpes virus 1 (HSV-1) and HSV-2 to acid and neutral pH (Zhong et al 2015; Huang et al 2014; Isaacs et al 2008; and De Oliveira et al 2013).

It is known that EGCG is a small molecule with the ability of covalent modification by non-specifically hydrogen binding to many proteins, which includes viral envelope glycoproteins, proteases, and cell receptors (Colpitts et al 2014; Ishii et al 2008; and Kaihatsu et al 2018). EGCG can covalently bind to cysteinyl thiol residues in the active center of many proteins, which may explain in part its extensive biological activity, particularly in several kinds of cancer cell lines. In addition, EGCG binds to glycosaminoglycans and to sialoglycans, which are constitutive part of the envelope of the vast majority of human viruses, including herpes simplex viruses, cytomegalovirus, influenza virus, poxvirus, hepatitis C virus, HIV, and many others. In fact, EGCG has been experimentally shown to have strong inactivating effects on enveloped virus such as influenza A virus by interfering with structural envelope glycoproteins that are key for viral adsorption. (Nakayama et al 1993; Furuta et al 2007; and Ling et al 2012) In regard to beta-coronavirus, there is experimental evidence that EGCG also has a potent inactivation activity against the enteric type of bovine beta-coronavirus (BCV), which uses its own spike protein (S) to propagate in cattle (Matsumoto et al 2005). By the use of hemagglutination assays and MDBK bovine kidney cells for studying virus-cell interactions, Matsumoto et al (2005) reported that BCV treated with EGCG, had a strong inhibitory effect on BCV propagation on cells untreated previously with EGCG. The authors reported that the direct antiviral inhibitory activity of EGCG on MDBK cells apparently was not as strong as the direct reactivity of EGCG to BCV. These results did demonstrate that the interaction between EGCG and the spike-glycoprotein S of BCV might play a pivotal role in the process of inhibition of viral entry exerted by EGCG during the first step of infection but does not rule out other potential direct or indirect effects during other phases of the coronavirus cycle within the host cells.

As part of the prior art, we found 24 international patent documents related to the use of EGCG for inhibiting several kinds of enveloped viruses such as influenza, HCV, HIV, rhinovirus, respiratory syncytial virus, etc. Regarding coronaviruses particularly, patent TW200533342A (Shau-Yi Liou et al 2005) provided evidence that catechins (including but not limited to EGCG), inhibited the replication of SARS-CoV in vero E6 cells. Patent JP2005314316A (Katayama et al 2005) provided experimental evidence that a composition of proanthocyanidin, catechins (including but not limited to EGCG) or a grape extract had antiviral activity against SARS coronavirus (SARS-CoV). Patent JPWO2006100710A1 (Kubo et al 2008) provided evidence that a daily dose of 50 mg/kg of body weight of a catechins-containing composition to 3 cynomolgus monkeys (compared to 3 controls, all infected intranasally and intratracheally with SARS-CoV) was able of suppressing the infection in 2 out of 3 treated monkeys, while all other 3 untreated monkeys and 1 treated monkey died. Patent CN105687226A (Chang Guohui et al 2013) provided experimental evidence that a composition of EGCG, tannic acid and *astragalus* polysaccharides may be used for suppressing infection of Mus hepatitis coronavirus A59 (MHV-A59). Patent EP1655292B1 (Furukawa et al 2015) provided evidence that EGCG had an effect to prevent BCV infection in MDBK cells. Finally, patent JP2018024610A (Yoshinaka et al 2018) provided experimental evidence that EGCG presents inhibitory activity against SARS coronavirus as well.

All coronaviruses encode a papaine-like protease (PLP) and a chymotrypsin-like (3CLPro also called Mpro) protease for proteolytic processing during virus replication (Báez-Santos et al 2015; Zhang et al 2020). Studies on other coronaviruses have shown that the PLP cleaves at two sites on the pp1a polyprotein and that the 3CLPro/Mpro protease cleaves at least 11 inter-domain sites on the pp1a and pp1ab polyproteins. Because both proteases are indispensable in the replication process of SARS-CoVs, PLP and 3CLpro/Mpro have been considered major molecular targets for anti-SARS drug discovery and developments. Direct in vitro experimental data of a strong inhibitory effect of EGCG on activity of 3CLpro from the first SARS-CoV have been recently provided by Nguyen et al with an active recombinant protease expressed in *Pichia pastoris*. EGCG displayed an IC50 of 73 μM and inhibited over 85% of the recombinant 3CLpro/Mpro. Interestingly, the galloyl moiety at 3-OH position was required for 3CLpro/Mpro inhibition activity (Nguyen et al 2012). Considering the very high homology of the 3CLpro/Mpro with the previous SARS coronavirus, this in vitro evidence is encouraging.

Innate immune system is the earliest and first line of antiviral defense against viruses. Coronaviruses like SARS and MERS are particularly skilled to evade immune detection and attenuating immune responses. It's not yet clear how SARS-CoV-2 affects the immune system, however apparently the latter resembles the evasive abilities from previous SARS-CoV. In fact, among all human coronaviruses, SARS-CoV exhibits the highest genome sequence identity (>80%) to SARS-CoV-2 (Wu et al 2020). Early evidence in vitro suggests that IFN-I effectively limit SARS-CoV-2 infection and therefore, these coronaviruses have evolved to inhibit IFN-I production and signaling during its replicative cycle (Vabret et al 2020). Experimental studies have identified two key SARS-CoVs proteins involved in this process of evasion of innate immune system such as PLP and N protein (Niemeyer et al 2018; Kopecky-Bromberg et al 2007; Surjit et al 2008). Interestingly both proteins, PLP and N appear prone to be counteracted by EGCG. Through the use of high-throughput screening nanoparticle-based RNA oligonucleotide biochip coated with recombinant N protein, Roh (2012) evaluated the inhibitory activity of 23 phenolic compounds including (−)-catechin, (−)-catechin gallate and (−)-gallocatechin gallate (the latter an epimer of EGCG). Only the two gallate compounds showed high inhibition activity in a concentrated manner and following a dose-response gradient against SARS-CoV N protein with an IC50 of 0.05 μg/mL$^{-1}$. In regard to PLP of SARS-CoV-2, Wu et al (2020), conducted a molecular docking study on PLP against an in-house library of 13 antiviral natural compounds and 78 known anti-viral drugs. EGCG and the antiviral drug ribavirin (the latter used in the treatment of patients with chronic HCV infection), were the inhibitors that exhibited the highest binding affinity to PLP core structure with the lowest energy scores. Noteworthy, EGCG and ribavirin have recently shown a significant improved clinical efficacy, safety, and tolerability when combined in the treatment of patients with HCV chronic disease (Shiha et al 2019). The latter is encouraging and provides an interesting therapeutic alternative to be explored in human SARS-CoV-2 infections.

Before the invention there was no direct experimental evidence of antiviral activity of EGCG on SARS-CoV-2 as part of the prior art. However, during 2021, three independent research groups provided experimental evidence that EGCG has direct antiviral activity on SARS-CoV-2. Firstly, Henss et al Gen Virol. 2021 April; 102:4) showed that EGCG blocked the entry of SARS-CoV-2 pseudotyped lentiviral vectors with IC50 values 2.47 μg ml$^{-1}$. In addition, EGCG inhibited virus replication at $IC_{50}$ 1.73 μg ml$^{-1}$ when replicating virus was used in Vero cells. Secondly, Hurst et al (*Microbiol Infect Dis.* 2021 April; 5(2): 1-6) demonstrated that EGCG at 0.27 μg/ml (0.59 μM) inhibited SARS-CoV-2 in Vero 76 cells by 50% (i.e., EC50=0.27 μg/ml). EGCG also inhibited SARS-CoV-2 infection in Caco-2 cells with EC90=28 μg/ml (61 μM). Finally, Hong et al (*J Agric Food Chem.* 2021 Jun. 2; 69(21): 5948-5954) screened natural compounds in vitro to identify inhibitors against Nsp15 enzyme from SARS-CoV-2. The authors confirmed a potent antiviral activity of EGCG in plaque reduction neutralization tests with a SARS-CoV-2 strain (PRNT50=0.20 μM; PRNT is the standard method for quantifying circulating levels of the antiviral neutralizing antibody).

Zinc as Antiviral Agent

Zinc (Zn) is a fundamental trace element provided by human diet and the second most abundant essential trace metal after Iron (Maxfield et al 2019; Thambiayya et al 2012). It is well known that over 99% of intracellular zinc is bonded to proteins such as metallothionein, glutathione, histidine, cysteine, and diphosphate compounds (Bozym et al 2006). In addition, because the concentration of intracellular zinc is tightly controlled in human cells by metallothionein (MT), zinc importers (ZIPs), zinc exporters (ZnTs) and specialized storing vesicles, the amount of free $Zn^{2+}$ ions is extremely limited (Bozym et al 2006; Colvin et al 2008). In fact, it is estimated that intracellular concentration of $Zn^{2+}$ is in the range of 10 μM to 10 nM. The latter remarks the importance of using active zinc-transporters or zinc-ionophores to induce a transient increase of the intracellular bioavailability of free/labile Zn and potentiate some desired biological effect in target cells (Dabbagh-Bazarbachi et al 2014).

The role of Zn on viral infections is a topic intensively investigated (Chauteverdi et al 2004; Prasad 2009) For example, in cell culture studies, Zn in combination with ionophore compounds (e.g. pyrithione) that may increase cellular import of free/labile $Zn^{2+}$ was found to inhibit the replication of various RNA viruses, including rhinovirus, (Krenn et al 2009) influenza virus, (Uchide et al 2002) and respiratory syncytial virus (Suara et al). These studies provided evidence that intracellular $Zn^{2+}$ levels may affect a common step in the replicative cycle of many viruses. There is clinical evidence that Zn supplementation may shorten the duration and intensity of symptoms of the common cold. One of the first double blind clinical studies by using Zn Gluconate (23 mg) for treatment of common cold, was conducted by Eby et al in 1985. In this study, after 7 days of treatment, 86% of 37 zinc-treated subjects were asymptomatic, compared with only 46% of 28 placebo-treated subjects.

Despite the obvious lack of clinical evidence about specific effects of Zn on SARS-CoV-2, some experimental evidence suggests that modulation of $Zn^{2+}$ status may be useful to counteract SARS-CoVs infections (Skalny et al 2020). As discussed above, PLP is essential for virus replication and evasion of innate immunity in host cells (Baéz-Santos et al 2015). In an elegant in vitro study with a fluorogenic inhibitor-screening platform, Han et al (2005) showed that $Zn^{2+}$ ions were capable of inhibiting PLP protease activity with an IC50 value of 1.3 μM. Two zinc conjugates, including N-ethyl-N-phenyl-dithio-carbamate-Zinc and 1-hydroxypridine-2-thione-Zinc were also effective in inhibiting SARS-CoV PLP, with the IC50 values of 3.3 and 3.7 μM, respectively. This inhibition was specific because other divalent metals, such as Mg, Mn, Ca, Ni, and Co, had no effects on the activity of PLP at 10 μM. Hsu et al (2004) screened a panel of metal ions including $Zn^{2+}$ and a conjugate 1-hydroxy-pyridine-2-thione-Zinc, confirming inhibitory activities on 3CLPro/Mpro, a key Cys protease for SARS-CoV replication in host cells as well. Interestingly, the Zn conjugate (i.e. a Zn salt) showed a strong competitive inhibition (Ki=0.17 μM) in comparison with $Zn^{2+}$ alone (Ki=1.1 μM). More recently, an interesting study by to Velthuis et al (2010) with live virus, demonstrated that the combination of $Zn^{2+}$ with the zinc-ionophore pyrithione (PT) at low concentrations (2 μM $Zn^{2+}$ and 2 μM PT) strongly inhibited the replication of SARS-coronavirus (SARS-CoV) in cell culture by interfering with the RNA-dependent RNA polymerase (RdRp). Specifically, $Zn^{2+}$ was found to block RdRp elongation. By using a strong Zn chelating agent, the inhibitory effect of $Zn^{2+}$ on RdRp activity was reversed.

Noteworthy, it is known EGCG forms stable chelated compounds (Alhafez et al 2019; Zhang et al 2015) with several metal ions, including Zn, and has recently been confirmed as potent zinc ionophore agent (Dabbagh-Bazarbachi et al 2014; Clergeaud et al 2016) EGCG interacts with cell membrane, decreasing the membrane fluidity of cells, and accelerates $Zn^{2+}$ accumulation in the mitochondria and cytosol (Yang et al 2009) Recently, an elegant study using an EGCG-ZnO complex and Zinquin fluorescent signals, was conducted to assess cellular uptake, intracellular trafficking, and disintegration of EGCG-ZnO nanoparticles on a prostate cancer cell line (PC-3). Interestingly, EGCG-ZnO particles entered cells via endocytosis and disintegrated inside the endosomal/lysosomal compartments, possibly due to the reduction of pH inside the vesicles. After that, EGCG and $Zn^{2+}$ were released into the cytoplasm and accumulated in the nucleus (Samutprasert et al 2018). In experiments on human liver cancer cell line (HepG2), EGCG appears inhibiting the expression of zinc-binding metallothioneins and plasma membrane $Zn^{2+}$ exporter ZnT1, while enhancing the expression of cellular $Zn^{2+}$ importers ZIP1 and ZIP4. EGCG also produced all these effects when HepG2 cells were stimulated to import $Zn^{2+}$ by treatment with supplemental Zn or the proinflammatory cytokine interleukin-6 (Quesada et al 2011).

DESCRIPTION OF THE DRAWINGS

(FIG. 12A).

Experimental scheme. Jurkat cells were transfected with viral RNA isolated from COVID-19 patients and incubated with EGCG-$Zn^{2+}$ complexes (Treated) or ST (Untreated). The proteins were extracted and analyzed by MS to investigate the changes induced by EGCG-$Zn^{2+}$ complexes on the host proteome by LFQ and on the translation of viral proteins by Single Reaction Monitoring (SRM); LC-MS/MS, Liquid Chromatography—tandem mass spectrometry; LFQ, Label Free Quantification. (FIG. 12B) Volcano plot of 3216 quantifiable proteins. The total number of proteins with significant abundance changes ($p<0.05$) comparing EGCG-$Zn^{2+}$ complexes (Treated) vs ST (Untreated). Proteins with significant high and low abundance are highlighted in red and blue, respectively. (FIG. 12C) Heatmap analysis of the 328 proteins with significant differential expression between cells stimulated EGCG-$Zn^{2+}$ complexes (Treated) vs ST (Untreated). The colors of the cells indicate the increase (red) or decrease (green) in the abundance of the protein. Abundance is defined as the logarithm in base 2 of the intensity standardized by the ST (Untreated). The groups correspond to cells treated with EGCG-$Zn^{2+}$ complexes (Treated) and ST (Untreated) in blue and red, respectively.

(FIG. 14A) Chromatogram of the GVYYPDK peptide corresponding to the Spike protein of SARS-CoV-2 measured in samples treated with EGCG-$Zn^{2+}$ complexes and control. The abundance parameter of the proteins in the sample is proportional to the intensity of the peptide. The colors of the lines account for the transitions of the measured forerunner. (FIG. 14B). The bar graph shows the intensity determined for the GVYYPDK peptide corresponding to the SARS-CoV-2 spike protein, in cells transfected with RNA isolated from COVID-19 patients and stimulated with EGCG-$Zn^{2+}$ complexes or control (untreated) bioinformatic analysis were performed using Skyline software. Statistical significance (**) was determined by applying a t-test.

FIG. 15. Cytotoxicity assay of EGCG-$Zn^{2+}$ complexes. The Jurkat cells were cultured in RPMI 1640 medium supplemented with 10% fetal bovine serum with IL2 supplementation until a confluence of 90%, subsequently 100,000 cells were used per experiment, which were treated with different concentrations of EGCG-$Zn^{2+}$ complexes and EGCG-$Zn^{2+}$ (1:3) complexes in triplicate (from 100 ug/ml to 1 ug/ml) additionally a control in triplicate containing the vehicle used for the preparation of the EGCG-$Zn^{2+}$ complexes, these were incubated for 24 h at 37° C. with 5% CO2. After the incubation time, the percentage of cell viability was measured using the Vybrant MTT Cell Proliferation Assay kit. The plate was measured at 570 nm using a spectrophotometer. The higher the value obtained, the greater the number of viable and metabolically active cells.

DETAILED DESCRIPTION OF THE INVENTION

Figure 1:
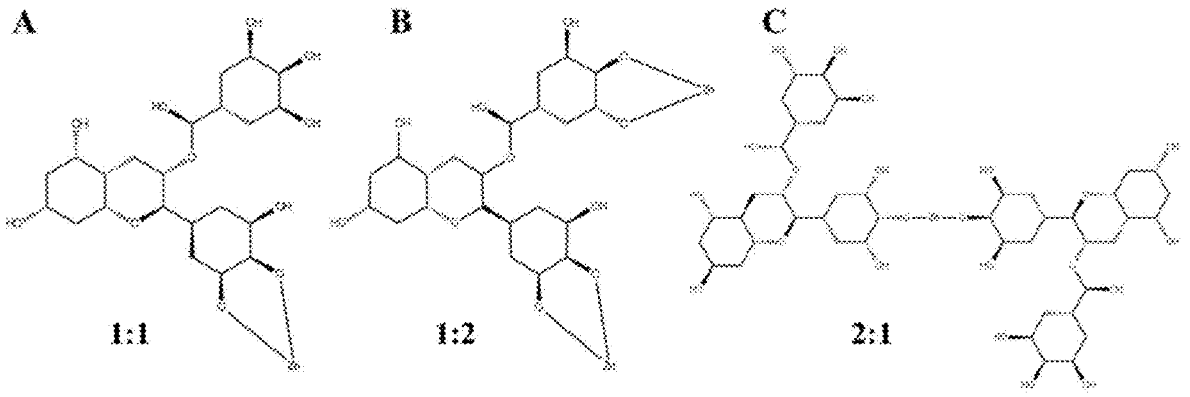
FIG. 1. Chemical description of EGCG-$Zn^{2+}$ complexes. The first species formed between EGCG and Zn corresponds to the formation of covalent bonds between the 2" and 3" hydroxyl groups with a $Zn^{2+}$ molecule as seen in FIG. 1A. The second species is given by the formation of bonds between the hydroxyl groups 2' and 3' with a Zn molecule and the hydroxyl groups 2" and 3" with another Zn molecule as shown in (FIG. 1B) and finally the third species is composed of two EGCG molecules coordinated with a Zn molecule in group 2" with 2" of each EGCG molecule (FIG. 1C).

A solid body of scientific evidence exposed above, suggests that both epigallocatechin-3-gallato (herein EGCG) or Zinc ($Zn^{2+}$) independently exhibit significant but still partial broad-spectrum antiviral activity. The invention consists in a formulation based on the extraordinary ability of EGCG to bind very efficiently Zn ions by chelation, forming coordinated covalent molecular compounds of EGCG-$Zn^{2+}$ (herein EGCG-$Zn^{2+}$ complexes) at physiological pH 7.4. This spontaneous, positive, stable, and strong interaction between EGCG and $Zn^{2+}$ produces ultimately a synergistic and highly effective antiviral mechanism potentiating the effects of both molecules against multiple molecular targets in several viruses, more particularly SARS-CoV-2, hampering or arresting almost completely the virus life cycle. The EGCG-$Zn^{2+}$ complexes can be used as a new method for chemoprophylaxis and treatment of coronavirus disease by using formulations containing a balanced composition of EGCG and $Zn^{2+}$ or EGCG-$Zn^{2+}$ complexes in sufficient amount to deliver a blood concentration with suppressive viral effect, minimizing safety issues in humans.

The present invention is directed to EGCG-$Zn^{2+}$ complexes with a high suppressive synergistic activity and low toxicity for the prevention and treatment of enveloped virus infections, including SARS-CoV-2, being said EGCG-$Zn^{2+}$ complexes represented by the formulae:

wherein these 3 complexes conformations were modeled in proportions EGCG-$Zn^{2+}$ of 1:1, 1:2 and 2:1. These complexes are formed at physiological pH as demonstrated in the examples. These complexes were demonstrated with a high suppressive synergistic activity and low toxicity for the prevention and treatment of a variety of enveloped viruses, including SARS-CoV-2.

In fact, it was demonstrated that EGCG-$Zn^{2+}$ complexes defined above are useful for the treatment of coronavirus disease 2019 (COVID-19) through different mechanisms, which can be listed as follows:

inhibiting viral reproduction in the host by binding of the compound to the ATPase site of NCP15 of the SARS-CoV-2, inhibiting viral reproduction in the host by deactivating the PLP complex of the SARS-CoV-2, inhibiting the interaction between the Spike protein of SARS-CoV-2 with the host ACE2 receptor of the SARS-CoV-2, interacting with the 3CLpro/Mpro protein of the SARS-CoV-2,

A

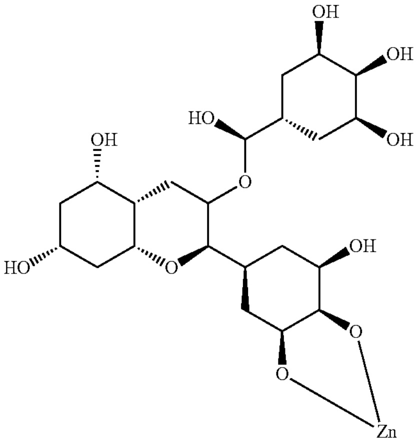

1:1

B

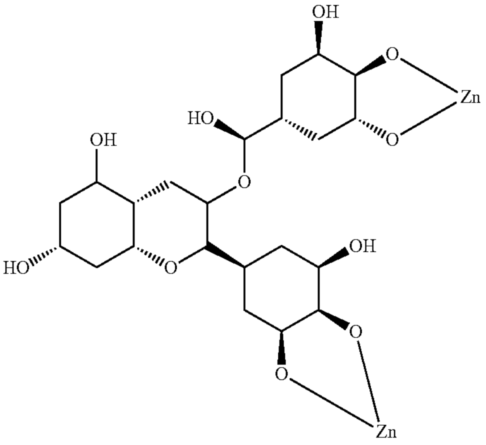

1:2

C

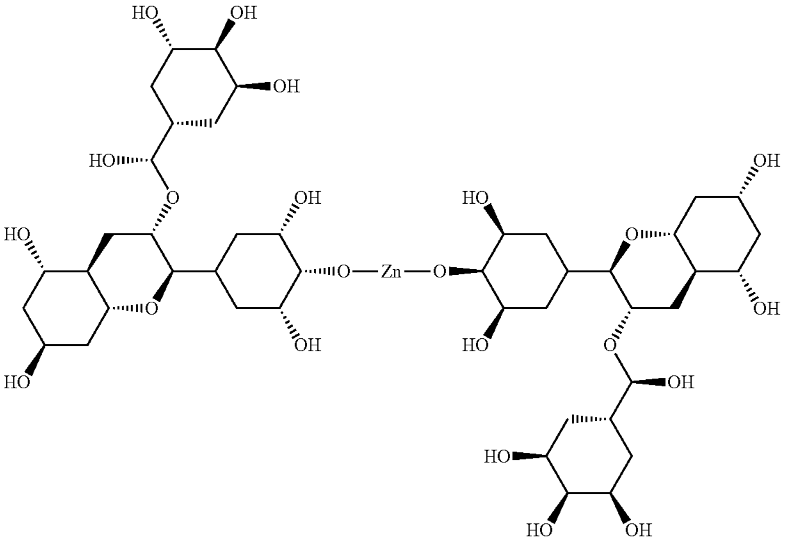

2:1 interacting with the RdRp protein of the SARS-CoV-2.

The present invention is also directed to an antiviral formulation containing any of the EGCG-$Zn^{2+}$ complexes. The source of $Zn^{2+}$ in these complexes can be a salt of zinc, consisting of zinc sulfate, zinc gluconate, zinc iodide, zinc chloride, zinc citrate, zinc carbonate, zinc hydroxide, zinc lactate, zinc acetate, zinc fluoride, zinc bromide, zinc sulfonate, zinc glucuronate, and zinc picolinate.

An antiviral formulation is also included within the scope of the invention. It is of a high preference that the complexes to be administered in the form of an oral dosage.

The EGCG-$Zn^{2+}$ complexes of the invention shown to be effective to carry out different treatments, as described as follows.

The EGCG-$Zn^{2+}$ complexes were shown effective for enhancing the antiviral effect and efficacy of EGCG and/or Zn. This method consists in providing at least once a day to a human or animal in need thereof, a formulation containing a combination of at least 10 mg up to 1000 mg of EGCG and at least 1 mg up to 30 mg of Zn in the form of EGCG-$Zn^{2+}$ complexes, during a time comprised at least between 1-3 days, preferably 1-10 days, more preferably 1-30 days, or less, finishing when the individual is considered healthy.

The complexes were also used in a method for the prevention or treatment of an infectious disease caused in humans by an enveloped virus, which method comprises providing at least once a day to an individual in need thereof, a formulation, which composition contains a combination of at least 10 mg up to 1000 mg of EGCG and at least 1 mg up to 30 mg of Zn in the form of EGCG-$Zn^{2+}$ complexes, during a time at least between 1-3 days, preferably 1-10 days, more preferably 1-30 days, or less, finishing when the individual is considered to be out of risk of infection or healthy.

The complexes were effective in a method for improving the bioavailability of EGCG for clinical use, and the method consists in providing at least once a day to a human or animal in need thereof, a formulation whose composition contains a combination of at least 10 mg up to 1000 mg of EGCG and at least 1 mg up to 30 mg of Zn in the form of EGCG-$Zn^{2+}$ complexes, during a time at least between 1-3 days, preferably 1-10 days, more preferably 1-30 days, or more in the case that it is necessary.

The complexes were also effective in a method for the prevention or treatment of immunologic complications from an infectious disease caused in humans by an enveloped virus. This method consists in providing at least once a day to an individual in need thereof, a formulation, which composition contains a combination of at least 10 mg up to 1000 mg of EGCG and at least 1 mg up to 30 mg of Zn in the form of EGCG-$Zn^{2+}$ complexes, during a time at least between 1-3 days, preferably 1-10 days, more preferably 1-30 days, or less. The treatment is finished when the individual is considered to be out of risk of immunologic complications or healthy.

A further method in which the complexes of the invention can be used is in decreasing toxicity, increasing at the same time the tolerability, and minimizing safety issues clinically. The method consists in providing at least once a day to an individual in need thereof, a formulation, which composition contains a combination of at least 10 mg up to 1000 mg of EGCG and at least 1 mg up to 30 mg of Zn in the form of EGCG-$Zn^{2+}$ complexes, during a time at least between 1-3 days, preferably 1-10 days, more preferably 1-30 days, or more in the case that it is necessary.

It must be taken into account that the low toxicity of the EGCG-$Zn^{2+}$ complexes allow methods with its extended administration, since the formulations are well tolerated showing a minimum of safety issues from the clinical point of view.

The invention also provides a method for treating an individual or patient, such a human being or animal, and the use of formulations containing a composition of EGCG and $Zn^{2+}$ in the form of EGCG-$Zn^{2+}$ complexes in a sufficient quantity, for the pre- and post-exposure prophylaxis of a disease caused in humans by emerging enveloped viruses, including SARS-CoV-2.

A wide variety of treating methods and uses were shown effective for the formulations containing the EGCG-$Zn^{2+}$ complexes of the present invention. Several methods and uses of such variety are effective in disorders involving shared mechanisms. The treatments are listed below:

- early treatment of a disease caused in humans by enveloped viruses, including SARS-CoV-2,
- to alleviate and shorten symptoms caused in humans by enveloped viruses, including SARS-CoV-2,
- as a complement or adjuvant to standard therapies used for the treatment of diseases caused in humans by enveloped viruses, including SARS-CoV-2,
- as inhibitor of the viral translation in experiments involving enveloped viruses, including SARS-CoV-2,
- as inhibitor of the viral adsorption in experiments involving enveloped viruses, including SARS-CoV-2,
- as inhibitor of the viral absorption in experiments involving enveloped viruses, including SARS-CoV-2,
- as inhibitor of the viral replication in experiments involving enveloped viruses, including SARS-CoV-2,
- as immunomodulatory agent in experiments involving infection by enveloped virus, including SARS-CoV-2,
- as inhibitor of the Papain-Like-Protein (PLP) of SARS-CoVs,
- as inhibitor of the main protease 3CLpro of SARS-CoVs,
- as inhibitor of the RNA dependent RNA polymerase (RdRp) of SARS-CoVs,
- as inhibitor of the Spike Protein (S) of SARS-CoVs,
- as inhibitor of the NSP15 of SARS-CoV-2 by interfering or blocking its active domain,
- as inhibitor of the domain RBD-ACE2 by interfering or blocking the viral adsorption of SARS-CoV-2,
- to be administered orally, intravenously, intramuscularly, endonasal, and subcutaneously for the treatment of a disease caused in humans by enveloped viruses, including SARS-CoV-2, to be administered as aerosol or nebulization for the treatment of a disease caused in humans by enveloped viruses, including SARS-CoV-2.

Although the above-mentioned forms of administration are possible and effective, the oral administration is the preferred one.

The expression "method of treating a patient" as employed in this description must be understood as including the prophylaxis or curative use of the EGCG-$Zn^{2+}$ complexes, and products, compositions and formulations containing the same, including the pre- and post-exposure prophylaxis of a disease caused in living individuals, such as humans or animals, by at least one virus, such as emerging enveloped viruses, including SARS-CoV-2.

The action mechanisms of the EGCG-$Zn^{2+}$ complexes are of a different nature, and they can be synthetized in specific inhibition mechanisms detailed in the following list:

- inhibition of the Papain-Like-Protein (PLP) of SARS-CoVs by interacting with the amino acids ASN-109A, GLY-160A, GLU-161A, LEU-162A, GLN-269A, GLN-160B, GLU-161B, LEU-162B, GLN-269B, HIS-89C, ASP-108C, ASN-109C, VAL-159C, GLY-160C, and GLN-269C, inhibition of the main protease 3CLpro of SARS-CoVs by interacting with the amino acids THR-26, LEU-27, HIS-41, MET-49, TYR-54, PHE-140, LEU-141, ASN-142, CYS-145, HIS-164, MET-165, GLU-166, ASP-187, ARG-188, and GLN-189, inhibition of the RNA dependent RNA polymerase (RdRp) of SARS-CoVs by interacting with the amino acids LEU-270, PRO-323, THR-324, PHE-326, PHE-396, and VAL-675, inhibition of the Spike Protein (S) of SARS-CoVs by interacting with the amino acids LEU-546A, THR-547A, ASP-568A, THR-572A, THR-573A, PRO-589A, MET-740B, TYR-741B, ILE-742B, CYS-743B, GLY-744B, ASP-745B, PHE-855B, ASN-856B, VAL-976B, ASN-978B, and ARG-1000B, inhibition of the NSP15 of SARS-CoV-2 by interfering or blocking its active domain made up of amino acids HIS-235, GLY-248, HIS-250, LYS-290, CYS-291, VAL-292, SER-294, TRP-333, THR-341, TYR-343, PRO-344, LYS-345, and LEU-346, inhibition of the NSP15 of SARS-CoV-2 by interfering or blocking the amino acids LYS-71, LYS-90, THR-167, THR-196, GLN-197, SER-198, ARG-199, ASN-200, LEU-252, ASP-273, SER-274, THR-275, LYS-277, TYR-279, VAL-295, ILE-296, and ASP-297, and inhibition of the domain RBD-ACE2 by interacting with the amino acids ILE-291, MET-366, ASP-367, LEU-370, THR-371, HIS-374, GLU-406, SER-409, LEU-410, PHE-438, GLN-442, and ILE-446.

The invention will be better described through the evidence provided in the following examples.

Example 1

EGCG Forms Complexes with Zinc at Physiological pH

Figure 2:
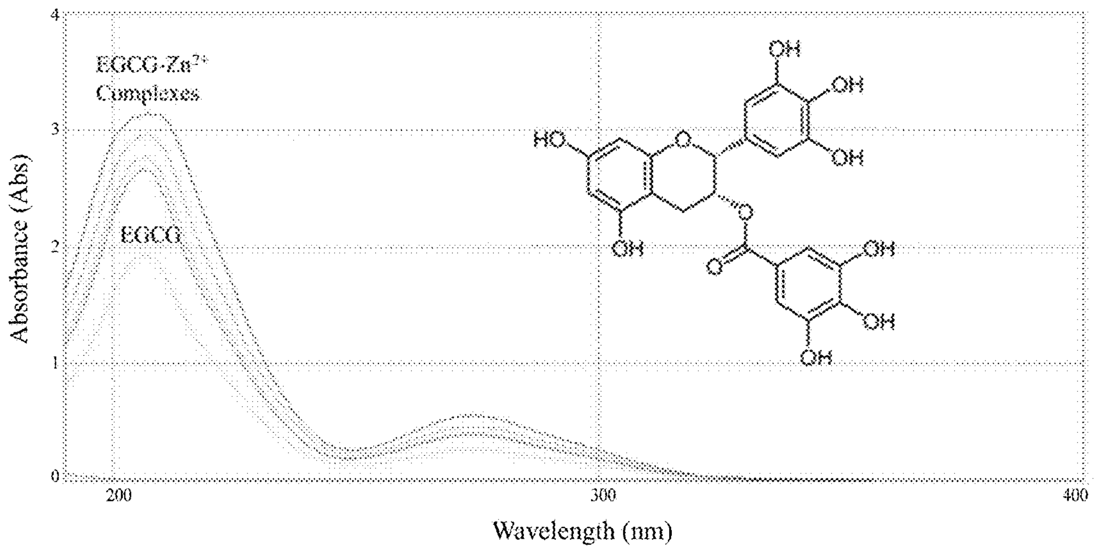
FIG. 2. UV/Vis spectrum of EGCG, EGCG-$Zn^{2+}$ complex proportion 1:1, and EGCG-$Zn^{2+}$ complex proportion 1:2 and 2:1 in the range 190 to 400 nm.
Figure 3:
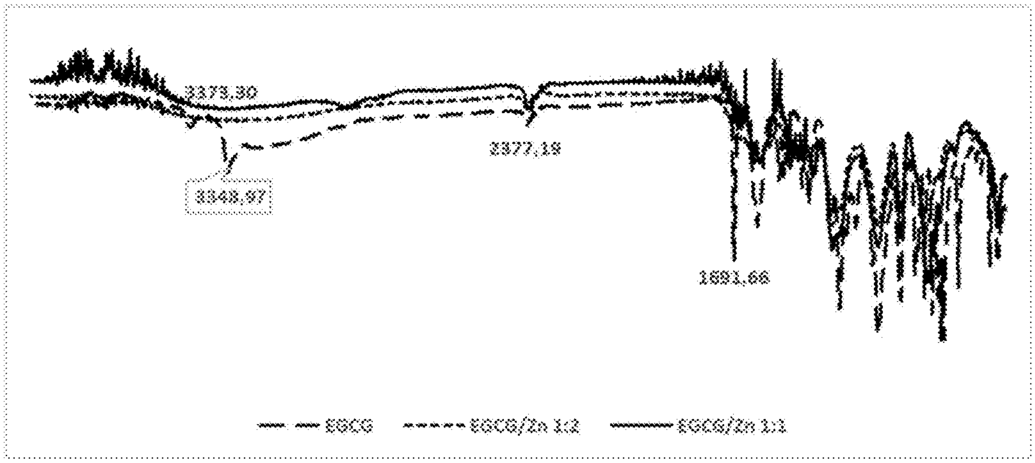
FIG. 3. Fourier transform infrared spectroscopy (FT-IR) of EGCG-$Zn^{2+}$ complex. EGCG (continuous line), complex EGCG-$Zn^{2+}$ 1:2 (dotted line), complex EGCG-$Zn^{2+}$ 1:1 (segment line). The spectrum was obtained in the range 800 to 4000 $cm^{-1}$, in the transmittance with 4 $cm^{-1}$ of resolution. The EGCG spectrum presents a strong Peak at 3474 $cm^{-1}$ and 3350 $cm^{-1}$ (0-H tension), which indicates that EGCG has hydroxyl groups. Other characteristic peaks are seen at 1690 $cm^{-1}$ tension (C═O) and 1614 $cm^{-1}$, 1446 $cm^{-1}$ (ring tension), 1342 $cm^{-1}$, 1213 $cm^{-1}$. (C—O tension), 1143 $cm^{-1}$ (C—H tension on the benzene ring). After the formation of the EGCG-$Zn^{2+}$ complex, several peaks were weakened, displaced, or disappeared. The EGCG peaks at 3474 $cm^{-1}$ and 3350 $cm^{-1}$ were significantly weakened, merged and changed at 3373 $cm^{-1}$, suggesting removal of the hydroxyl group in EGCG-$Zn^{2+}$, and the 1690 $cm^{-1}$ peak disappeared and merged with the 1614 $cm^{-1}$ to form a new peak at 1607 $cm^{-1}$, the peaks at 1543 $cm^{-1}$ and 1525 $cm^{-1}$ were merged to form a new peak at 1507 $cm^{-1}$. This result confirms the formation of the EGCG-$Zn^{2+}$ complexes.
Figure 4:
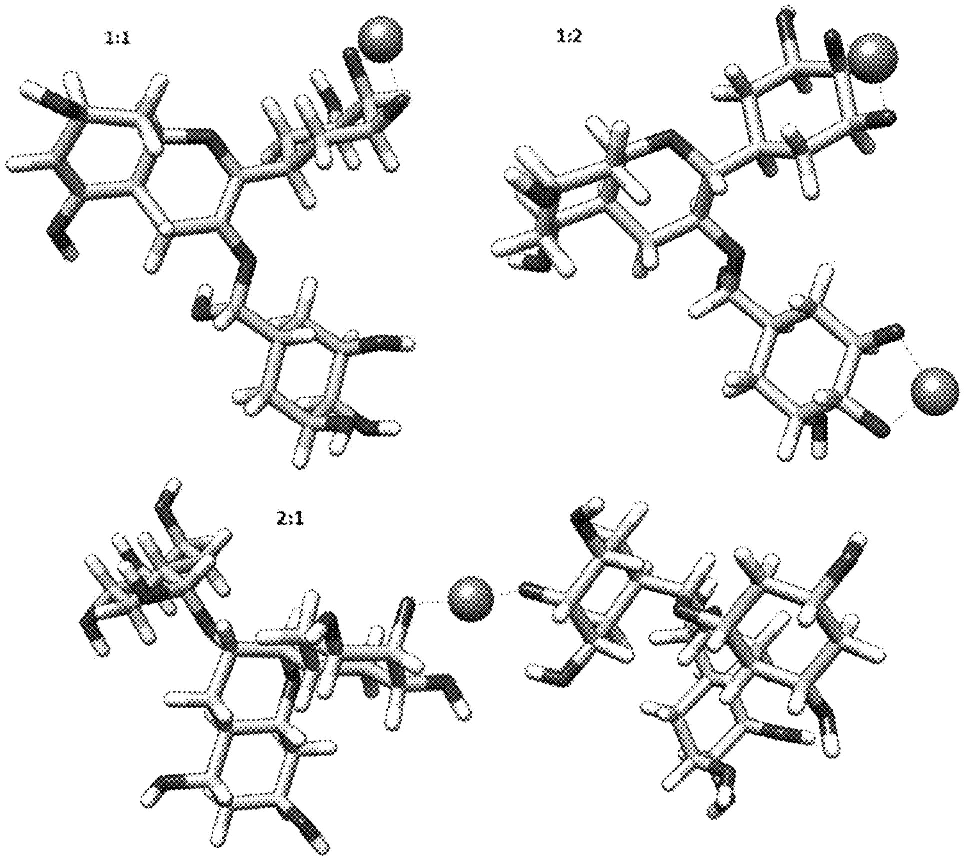
FIG. 4. The 3D structure of the ligand. EGCG was obtained from PubChem under the identifier 65064. The structures of EGCG-$Zn^{2+}$ complexes were modeled by means of the Avogadro software. Three possible conformations of EGCG and $Zn^{2+}$ were modeled, in the proportions: 1:1, 1:2 and 2:1. Hydrogens were added to all conformations to comply with the octet rule, in addition each structure was energetically minimized through the self-optimization tool and using a universal force field. Structures of the 3D conformations of EGCG-$Zn^{2+}$ complexes. Each structure is made up of different proportions of EGCG and $Zn^{2+}$. The 1:1 ratio refers to the structure with an EGCG molecule and a Zinc ion. The 1:2 ratio refers to the structure with one EGCG molecule and two Zinc ions. The 2:1 ratio refers to the structure with two EGCG molecules and one Zinc ion.

Briefly, a 10 mM EGCG solution was stirred at 750 rpm at 20° C. under the protection of nitrogen. Meanwhile, 10 mM zinc chloride was slowly added to the EGCG solution in a 2:1 molar ratio. The pH of the mixture was adjusted to 7.4 by adding 10 mM $NaHCO_3$. Next, the products formed were collected by centrifugation, washed with deionized water, and lyophilized until the dry EGCG-$Zn^{2+}$ complex was obtained. The resulting complex was analyzed by FT-IR, with ATR in the range of 800 to 4000 in transmittance, and the absorbance was measured with UV/Vis spectrophotometer, in the range of 190 to 900 nm. We have proposed the formation of at least 3 complex species between EGCG and $Zn^{2+}$, which are outlined in FIG. 1 and FIG. 4. In addition, changes are observed in the UV-Vis absorption spectra of EGCG compared to the complexes formed, where changes are seen in the 216 nm which are increased in the complexes formed, as seen in FIG. 2. It was observed that the EGCG FT-IR spectrum presents a strong Peak at 3474 $cm^{-1}$ and 3350 $cm^{-1}$ (0-H tension), which indicates that EGCG has hydroxyl groups. Other characteristic peaks are seen at 1690 $cm^{-1}$ tension (C═O) and 1614 $cm^{-1}$, 1446 $cm^{-1}$ (ring tension), 1342 $cm^{-1}$, 1213 $cm^{-1}$. (C—O tension), 1143 $cm^{-1}$ (C—H tension on the benzene ring). After the formation of the EGCG-$Zn^{2+}$ complex, several peaks were weakened, displaced, or disappeared. The EGCG peaks at 3474 $cm^{-1}$ and 3350 $cm^{-1}$ were significantly weakened, merged and changed at 3373 $cm^{-1}$, suggesting removal of the hydroxyl group in EGCG-$Zn^{2+}$, and the 1690 $cm^{-1}$ peak disappeared and merged with the 1614 $cm^{-1}$ to form a new peak at 1607 $cm^{-1}$, the peaks at 1543 $cm^{-1}$ and 1525 $cm^{-1}$ were merged to form a new peak at 1507 $cm^{-1}$. This result confirms the formation of the EGCG-$Zn^{2+}$ complexes (FIG. 3).

METHOD (for Example 2 to Example 8)

1.1 Obtaining Proteins Structures and Small Molecules for Docking Assays

The selected ligands for the molecular docking experiment were EGCG molecule alone, Zn gluconate molecule alone and EGCG-$Zn^{2+}$ complexes. The 3D structure of EGCG and Zinc gluconate was obtained from PubChem, under the identifier "65064" and "443445", respectively. The structures of EGCG-$Zn^{2+}$ complexes were modeled through Avogadro software. Three possible conformations of EGCG-$Zn^{2+}$ were modeled in proportions: 1:1, 1:2 and 2:1. Hydrogens were added to all conformations to comply with the octet rule, in addition, each structure was energetically minimized through the self-optimization tool and using a universal force field. Protein structures of SARS-CoV-2 were obtained from the RCSB Protein Data Bank (PDB) database. The PDB files used correspond to: 3CLpro (PDB: 6LU7), ACE2 Receptor with RBD spike (PDB: 6M0J), PLP (PDB: 6W9C), RdRp (PDB: 6M71), Spike Protein (PDB: 6VXX) and Endoribonuclease NSP15 (PDB: 6W01).

1.2 Receptor Minimization

First, all non-standard residues, native ligands, and water molecules were removed from each of the protein structures. The resulting structures were initially prepared through structural minimization, considering 200 "steepest descent steps" with a "step size" of 0.02 A and 20 steps of conjugated gradients with 0.02 A "step size". Hydrogen atoms and charges were added using the Dunbrack 2010 rotamer library. Charges were analyzed by ANTERCHAMBER using the AM1-BCC charge method. These processes were performed using the USCF Chimera software. All the resulting structures were saved in .pdb format files.

1.3 Interaction Zone Selection

Probable binding sites were predicted using AutoSite 1.0 of AutoGridFR software, part of the AutoDockFR software suite. Each binding sites were predicted with default parameters. In addition, the amino acids that interact with the native ligands of the proteins were considered. The coordinates and the size of the binding site, calculated with AutoSite 1.0, were used for the molecular docking of EGCG-$Zn^{2+}$ complex, against each chosen receptor. The amino acids of binding site of each receptor are shown in table 1, where the distance between the ligands and near amino acids were 8 A, approximately.

TABLE 1

| Amino acids involved in the docking site of EGCG-$Zn^{2+}$ complexes | |
|---|---|
| Docking complex | Amino acid in docking box |
| PLP | HIS-89A ALA-107A ASP-108A ASN-109A LYS-157A THR-158A VAL-159A GLY-160A GLU-161A LEU-162A GLY-163A TYR-268A GLN-269A CYS-270A GLY-271A HIS-272A HIS-89B ALA-107B ASP-108B ASN-109B LYS-157B THR-158B VAL-159B GLY-160B GLU-161B LEU-162B GLY-163B TYR-268B GLN-269B CYS-270B GLY-271B HIS-272B HIS-89C ALA-107C ASP-108C ASN-109C LYS-157C THR-158C VAL-159C GLY-160C GLU-161C LEU-162C GLY-163C TYR-268C GLN-269C CYS-270C GLY-271C HIS-272C |
| RdRp | ASP-269 LEU-270 LEU-271 LYS-272 TYR-273 ASP-274 PRO-322 PRO-323 THR-324 SER-325 PHE-326 GLY-327 PRO-328 LEU-329 VAL-330 HIS-347 TYR-346 PRO-378 ALA-379 MET-380 ALA-383 ALA-382 ALA-399 VAL-398 SER-397 PHE-396 SER-664 GLU-665 MET-666 VAL-667 TYR-674 VAL-675 LYS-676 PRO-677 GLY-678 |
| ACE2-RBD | LYS-288 PRO-289 ASN-290 ILE-291 ASP-292 VAL-293 THR-365 MET-366 ASP-367 ASP-368 PHE-369 LEU-370 THR-371 ALA-372 HIS-373 HIS-374 GLU-375 GLU-405 GLU-406 ILE-407 MET-408 SER-409 LEU-410 SER-411 ALA-412 ALA-413 THR-414 ILE-436 ASN-437 PHE-438 LEU-439 LEU-440 LYS-441 GLN-442 ALA-443 LEU-444 THR-445 ILE-446 |
| 3CLpro | THR-24 THR-25 THR-26 LEU-27 PRO-39 ARG-40 HIS-41 VAL-42 ILE-43 CYS-44 THR-45 SER-46 GLU-47 ASP-48 MET-49 LEU-50 ASN-51 TYR-54 SER-139 PHE-140 LEU-141 ASN-142 GLY-143 SER-144 CYS-145 HIS-163 HIS-164 MET-165 GLU-166 LEU-167 VAL-186 ASP-187 ARG-188 GLN-189 THR-190 ALA-191 |
| NSP15 Active Site | HIS-235 GLN-245 LEU-246 GLY-247 GLY-248 LEU-249 HIS-250 SER-289 LYS-290 CYS-291 VAL-292 CYS-293 SER-294 THR-341 PHE-342 TYR-343 PRO-344 LYS-345 LEU-346 |
| NSP15 Alternative Site | LYS-71 LYS-90 GLY-165 VAL-166 THR-167 LEU-168 THR-196 GLN-197 SER-198 ARG-199 ASN-200 LEU-201 GLN-202 HIS-250 LEU-251 LEU-252 ILE-253 GLU-265 LEU-266 GLU-267 ASP-268 PHE-269 ILE-270 PRO-271 MET-272 ASP-273 SER-274 THR-275 VAL-276 LYS-277 ASN-278 TYR-279 SER-294 VAL-295 ILE-296 ASP-297 LEU-298 |
| Spike | LEU-546A THR-547A GLY-548A THR-549A GLY-550A VAL-551A ARG-567A ASP-568A ILE-569A ALA-570A ASP-571A THR-572A THR-573A ASP-574A ASP-586A ILE-587A THR-588A PRO-589A CYS-590A SER-591A MET-740B TYR-741B ILE-742B CYS-743B GLY-744B ASP-745B PHE-855B ASN-856B GLY-857B LEU-966B SER-967B VAL-976B LEU-977B ASN-978B ASP-979B |

1.4 Molecular Docking

The 3 conformations of EGCG-$Zn^{2+}$ complexes, EGCG molecule alone and Zinc gluconate molecule alone were used for molecular docking with all the chosen receptors. The molecular docking study was performed with USCF Chimera software using an Autodock Vina implementation. The interaction site was created by means of the coordinates obtained previously through AutoGridFR. A total of 10 binding modes were generated. Each docking was repeated 10 times. The best docking scores (binding energy) were exported in pdb format and created the receptor-ligand complex to be visualized in USCF Chimera software.

Example 2

Figure 5:
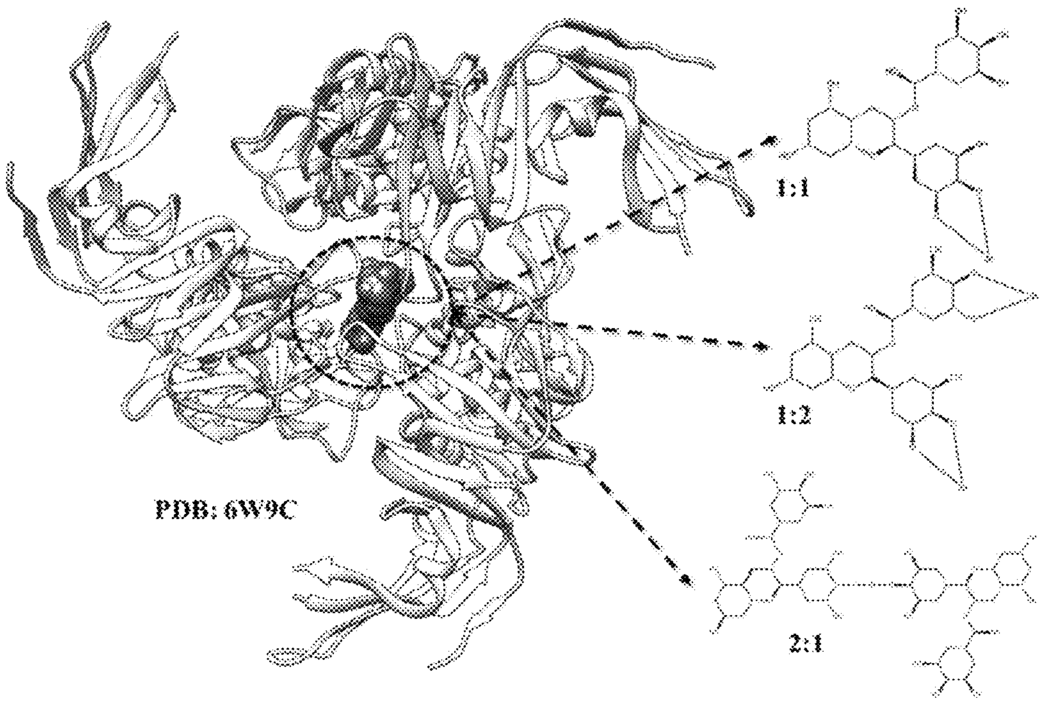
FIG. 5. SARS-CoV-2 Papain-like protease (PLP) protein structure proposed as therapeutic target for EGCG-$Zn^{2+}$ complexes. The protein considered is PLP protein, PDB code: 6W9C. The black circle refers to the interaction site with the three conformations of the EGCG-$Zn^{2+}$ complexes (1:1, 1:2 and 2:1 ratio).

EGCG-$Zn^{2+}$ Complexes Interact with Papain-Like Protease (PLP) of SARS-CoV-2 with More Favorable Energies than EGCG Molecule Alone or Zn Molecule Alone Multiple molecular docking analyzes, using 3 conformations of EGCG-$Zn^{2+}$ complexes and the Papain-like protease of SARS-CoV-2, indicate that the binding energy is favorable (FIG. 5). Considering the conformation of EGCG-$Zn^{2+}$ complexes 1:1 (1 EGCG: 1 $Zn^{2+}$), the binding energies obtained was −9.3 Kcal/mol. For the conformation of EGCG-$Zn^{2+}$ complexes 2:1 (2 EGCG: 1 $Zn^{2+}$), the binding energies with PLP were −10.1 Kcal/mol. For the conformation of EGCG-$Zn^{2+}$ complexes 1:2 (1 EGCG: 2 $Zn^{2+}$), the binding energies with PLP were −9.6 Kcal/mol. Using the same methodology, for the EGCG molecule alone and Zinc gluconate alone, the binding energy with PLP were −8.6 Kcal/mol and −6.0 Kcal/mol, respectively. The binding energies obtained reflect the in-silico feasibility of forming the PLP-EGCG-$Zn^{2+}$ complexes protein complex (Table 2), producing hydrophobic interactions, hydrogen bonds and salt bridges in the docking analysis. Table 3 shows the amino acids with which the ligands interact in each of the predicted pockets of each protein receptor. It should be noted that the docking analysis performed with the EGCG-$Zn^{2+}$ complexes present much more favorable energies than the analyzes performed only with EGCG molecule or Zn molecule alone; this allows us to infer that possibly the EGCG-$Zn^{2+}$ complexes will have a greater effect than EGCG, in-vivo.

Example 3

Figure 6:
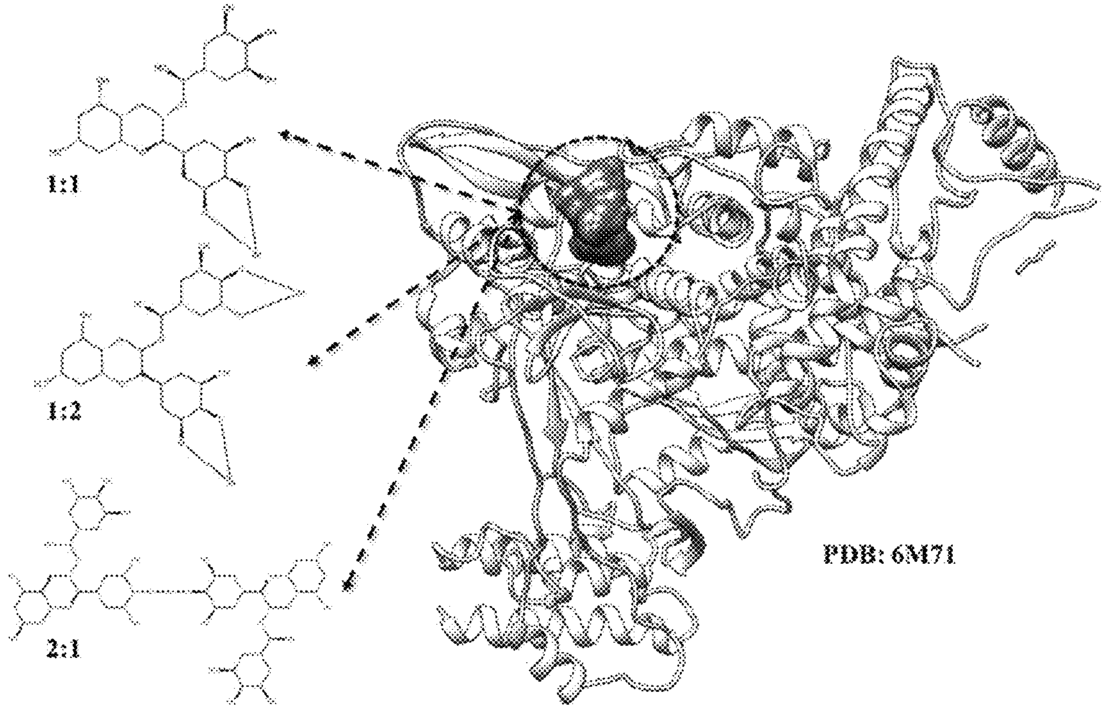
FIG. 6. SARS-CoV-2 RNA-dependent RNA polymerase protein structure proposed as therapeutic target for EGCG-$Zn^{2+}$ complexes. The protein considered is RNA-dependent RNA polymerase (RdRp), PDB code: 6M71. The black circle refers to the interaction site with the three conformations of the EGCG-$Zn^{2+}$ complexes (1:1, 1:2 and 2:1 ratio).

EGCG-$Zn^{2+}$ Complexes Interact with RNA-Dependent RNA Polymerase Protein (RdRp) of SARS-CoV-2 with More Favorable Energies than EGCG Molecule Alone or Zn Molecule Alone New molecular docking analyzes, using 3 conformations of EGCG-$Zn^{2+}$ complexes and the RNA-dependent RNA polymerase (RdRp) of SARS-CoV-2, indicate that the binding energy is favorable (FIG. 6). Considering the conformation of EGCG-$Zn^{2+}$ complexes 1:1 (1 EGCG: 1 $Zn^{2+}$), the binding energies obtained were −7.5 Kcal/mol. For the conformation of EGCG-$Zn^{2+}$ complexes 2:1 (2 EGCG: 1

Zn+2), the binding energies obtained were −9.6 Kcal/mol. For the conformation of EGCG-$Zn^{2+}$ complexes 1:2 (1 EGCG: 2 $Zn^{2+}$), the binding energies obtained were −8.3 Kcal/mol. Using the same methodology, for the EGCG molecule alone and Zinc gluconate alone, the binding energy obtained were −7.3 Kcal/mol and −6.5 Kcal/mol, respectively. The binding energies obtained reflect the in-silico feasibility of forming the RdRp-EGCG-$Zn^{2+}$ complexes protein complex (Table 2), producing hydrophobic interactions, hydrogen bonds and salt bridges in the docking analysis. Table 3 shows the amino acids with which the ligands interact in each of the predicted pockets of each protein receptor. It should be noted that the docking analysis performed with the EGCG-$Zn^{2+}$ complexes present much more favorable energies than the analyzes performed only with EGCG molecule or Zn molecule alone; this allows us to infer that possibly the EGCG-$Zn^{2+}$ complexes will have a greater effect than EGCG, in-vivo.

Example 4

Figure 7:
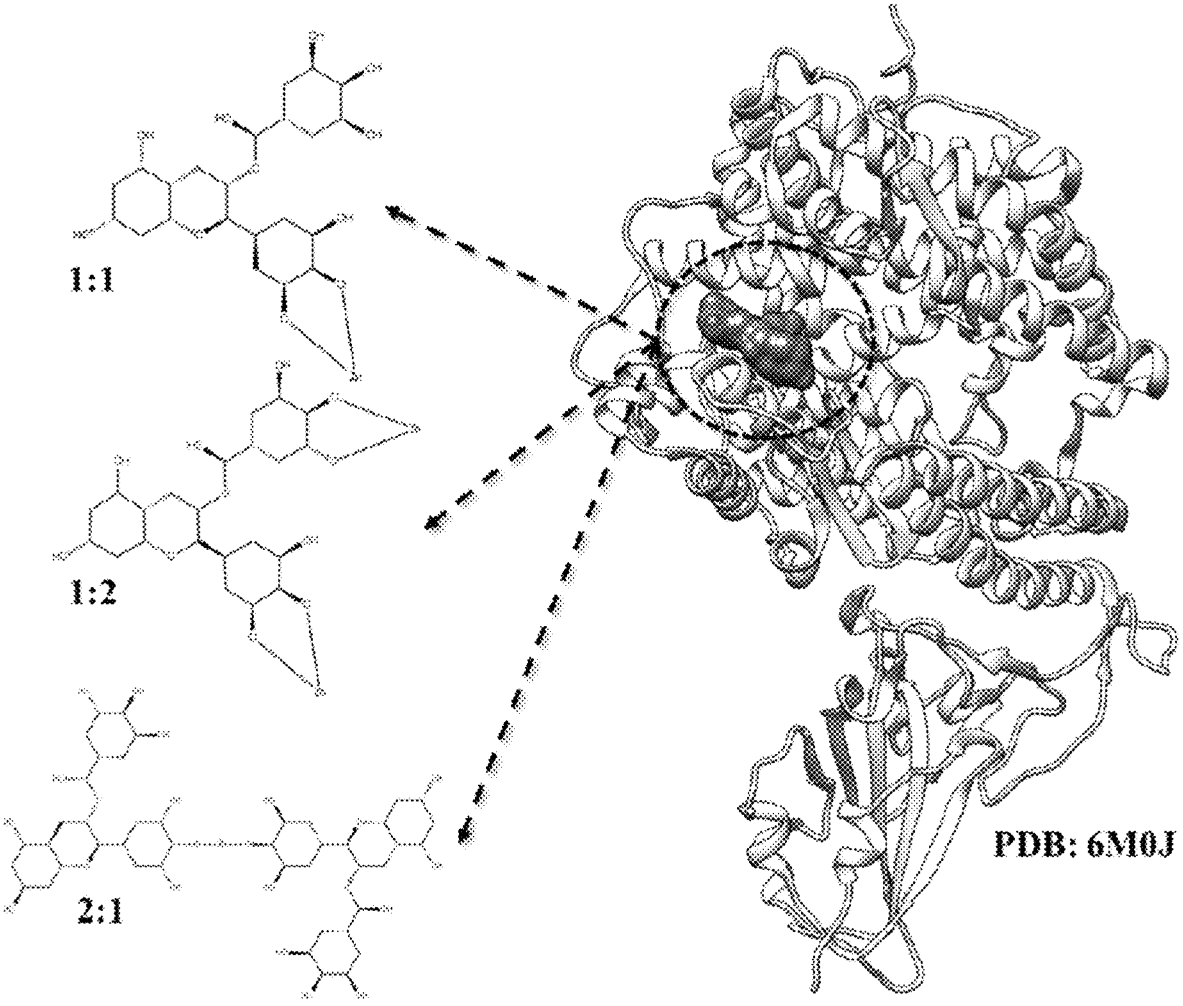
FIG. 7. Angiotensin Converting Enzyme 2 (ACE2) receptor with Receptor Binding Domain of Spike protein (RBD) proposed as therapeutic targets. The proteins complex considered are ACE2-RBD, PDB code: 6M0J. The black circle refers to the interaction site with the three conformations of the EGCG-$Zn^{2+}$ complexes (1:1, 1:2 and 2:1 ratio).

EGCG-$Zn^{2+}$ Complexes Interact with Angiotensin Converting Enzyme 2 Receptor with Receptor Binding Domain of Spike Protein Complex (ACE2-RBD) with More Favorable Energies than EGCG Molecule Alone or Zn Molecule Alone New molecular docking analyzes, using 3 conformations of EGCG-$Zn^{2+}$ complexes and the Angiotensin Converting Enzyme 2 (ACE2) receptor with Receptor Binding Domain (RBD) of Spike protein complex from SARS-CoV-2, indicate that the binding energy is favorable (FIG. 7). Considering the conformation of EGCG-$Zn^{2+}$ complexes 1:1 (1 EGCG: 1 $Zn^{2+}$), the binding energies obtained were −7.7 Kcal/mol. For the conformation of EGCG-$Zn^{2+}$ complexes 2:1 (2 EGCG: 1 $Zn^{2+}$), the binding energies obtained were −9.1 Kcal/mol. For the conformation of EGCG-$Zn^{2+}$ complexes 1:2 (1 EGCG: 2 $Zn^{2+}$), the binding energies obtained were −8.3 Kcal/mol. Using the same methodology, for the EGCG molecule alone and Zinc gluconate molecule alone, the binding energy obtained were −7.6 Kcal/mol and −6.0 Kcal/mol, respectively. The binding energies obtained reflect the in-silico feasibility of creating the ACE2-RBD-EGCG-$Zn^{2+}$ complexes protein complex (Table 2), producing hydrophobic interactions, hydrogen bonds and salt bridges in the docking analysis. Table 3 shows the amino acids with which the ligands interact in each of the predicted pockets of each protein receptor. It should be noted that the docking analysis performed with the EGCG-$Zn^{2+}$ complexes present much more favorable energies than the analyzes performed only with EGCG molecule or Zn molecule alone; this allows us to infer that possibly the EGCG-$Zn^{2+}$ complexes will have a greater effect than EGCG, in-vivo.

Example 5

Figure 8:
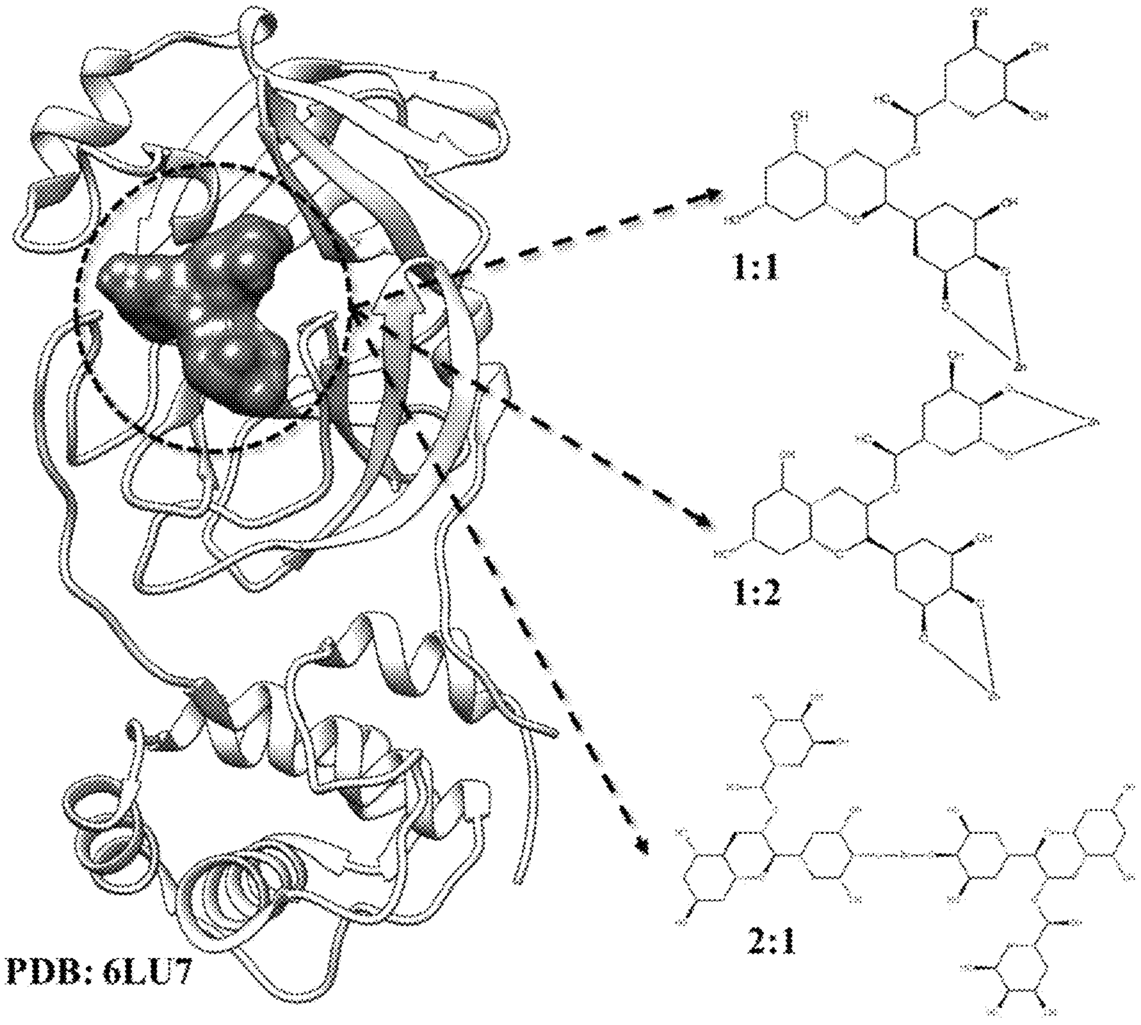
FIG. 8. SARS-CoV-2 3-Chymotrypsin like protease (3CLpro) protein structure proposed as therapeutic target. The protein considered is 3CLpro, PDB core: 6LU7. The black circle refers to the interaction site with the three conformations of the EGCG-$Zn^{2+}$ complexes (1:1, 1:2 and 2:1 ratio).

EGCG-$Zn^{2+}$ Complexes Interact with 3-Chymotrypsin-Like Protease (3CLpro) of SARS-CoV-2 with More Favorable Energies than EGCG Molecule Alone or Zn Molecule Alone New molecular docking analyzes, using 3 conformations of EGCG-$Zn^{2+}$ complexes and the 3-Chymotrypsin-like protease of SARS-CoV-2, indicate that the binding energy is favorable (FIG. 8). Considering the conformation of EGCG-$Zn^{2+}$ complexes 1:1 (1 EGCG: 1 $Zn^{2+}$), the binding energies obtained were −9.0 Kcal/mol. For the conformation of EGCG-$Zn^{2+}$ complexes 2:1 (2 EGCG: 1 $Zn^{2+}$), the binding energies obtained were −8.8 Kcal/mol. For the conformation of EGCG-$Zn^{2+}$ complexes 1:2 (1 EGCG: 2 $Zn^{2+}$), the binding energies obtained were −9.6 Kcal/mol. Using the same methodology, for the EGCG molecule alone and zinc gluconate molecule alone, the binding energy obtained were −7.9 Kcal/mol and −6.3 Kcal/mol, respectively. The binding energies obtained reflect the in-silico feasibility of creating the 3CLpro-EGCG-$Zn^{2+}$ complexes protein complex (Table 2), producing hydrophobic interactions, hydrogen bonds and salt bridges in the docking analysis. Table 3 shows the amino acids with which the ligands interact in each of the predicted pockets of each protein receptor. It should be noted that the docking analysis performed with the EGCG-$Zn^{2+}$ complexes present much more favorable energies than the analyzes performed only with EGCG molecule or Zn molecule alone; this allows us to infer that possibly the EGCG-$Zn^{2+}$ complexes will have a greater effect than EGCG, in-vivo.

TABLE 2

Summary of binding energies reported in the formation of protein-ligand complexes

| SARS CoV-2 | | (EGCG—$Zn^{2+}$ Complex) (Kcal/mol) | | | EGCG (Kcal/mol) | Zinc Gluconate (Kcal/mol) |
|---|---|---|---|---|---|---|
| Template | PDB | 1:1 | 2:1 | 1:2 | 1:1 | 1:1 |
| 3CLpro | 6LU7 | −9.0 | −8.8 | −9.6 | −7.9 | −6.3 |
| Spike | 6VXX | −8.9 | −9.2 | −8.4 | −8.4 | −6.2 |
| PLP | 6W9C | −9.3 | −10.1 | −9.6 | −8.6 | −6.0 |
| RdRp | 6M7I | −7.5 | −9.6 | −8.3 | −7.3 | −6.5 |
| ACE2-RBD | 6M0J | −7.7 | −9.1 | −8.3 | −7.6 | −6.0 |
| NSP15—Alternative site | 6VWW | −8.9 | −9.9 | −9.2 | −8.8 | −7.2 |
| NSP15—Active site | 6VWW | −7.7 | −8.2 | −7.9 | −7.0 | −6.6 |

Example 6

Figure 9:
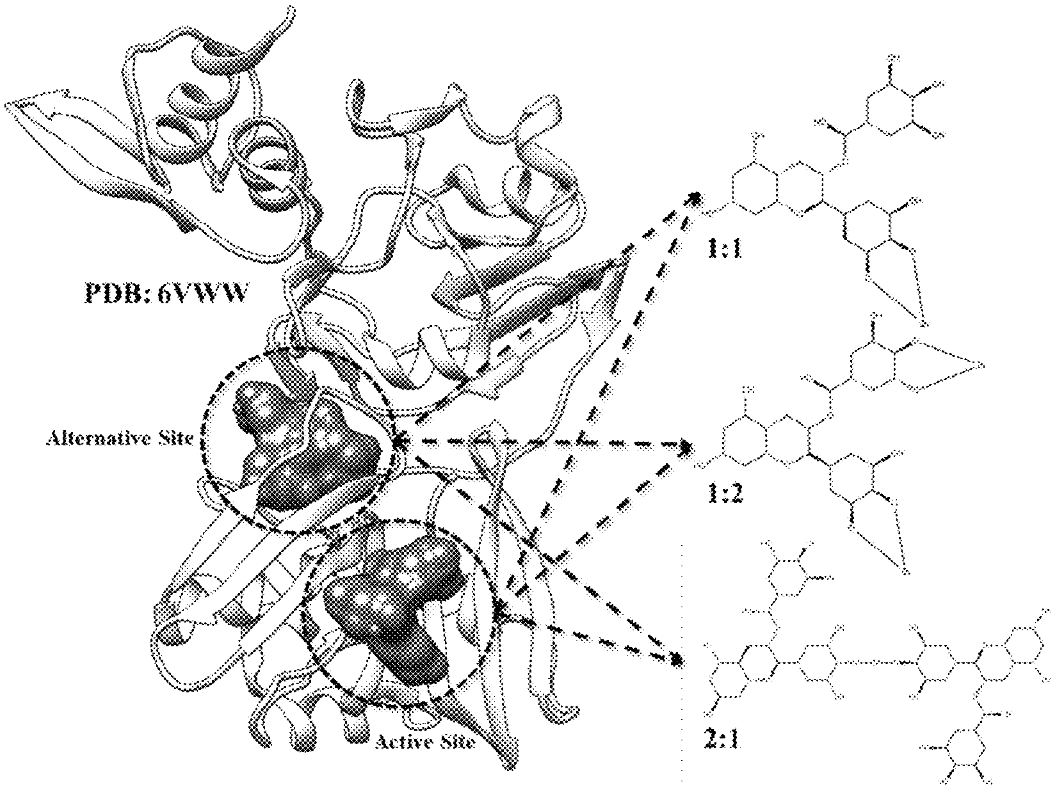
FIG. 9. SARS-CoV-2 Endoribonuclease Nsp15 protein structure proposed as therapeutic target. The protein considered is NSP15, PDB code: 6VWW. The black circle refers to the interaction site with the three conformations of the EGCG-$Zn^{2+}$ complexes (1:1, 1:2 and 2:1 ratio).

EGCG-$Zn^{2+}$ Complexes Interact with Endoribonuclease NSP15 of SARS-CoV-2 with More Favorable Energies than EGCG Molecule Alone or Zn Molecule Alone New molecular docking analyzes, using 3 conformations of EGCG-$Zn^{2+}$ complexes and the Endoribonuclease NSP15 of SARS-CoV-2, indicate that the binding energy is favorable (FIG. 9). Considering the conformation of EGCG-$Zn^{2+}$ complexes 1:1 (1 EGCG: 1 $Zn^{2+}$), the binding energies obtained were −7.7 Kcal/mol in the active site and −8.9 Kcal/mol in an alternative site. For the conformation of EGCG-$Zn^{2+}$ complexes 2:1 (2 EGCG: 1 $Zn^{2+}$), the binding energies obtained were: −8.2 Kcal/mol in the active site and −9.9 Kcal/mol in an alternative site. For the conformation of EGCG-$Zn^{2+}$ complexes 1:2 (1 EGCG: 2 $Zn^{2+}$), the binding energies obtained were: −7.9 Kcal/mol in the active site and −9.2 Kcal/mol in an alternative site. Using the same methodology, for the EGCG molecule alone and zinc gluconate molecule alone, the binding energy obtained in the active site were −7.0 Kcal/mol and −6.6 Kcal/mol, respectively, and the binding energy obtained in an alternative site were −8.8 Kcal/mol and −7.2 Kcal/mol, respectively. The binding energies obtained reflect the in-silico feasibility of creating the NSP15-EGCG-$Zn^{2+}$ complexes protein complex (Table 2), producing hydrophobic interactions, hydrogen bonds and salt bridges in the docking analysis. Table 3 shows the amino acids with which the ligands interact in each of the predicted pockets of each protein receptor. It should be noted that the docking analysis performed with the EGCG-$Zn^{2+}$ complexes present much more favorable energies than the analyzes performed only with EGCG molecule or Zn molecule alone; this allows us to infer that possibly the EGCG-$Zn^{2+}$ complexes will have a greater effect than EGCG, in-vivo.

TABLE 3

| Amino acids that interact with the EGCG-$Zn^{2+}$ complexes | |
|---|---|
| Docking Complex | Interacting Amino acid |
| PLP | ASN-109A GLY-160A GLU-161A LEU-162A GLN-269A GLN-160B GLU-161B LEU-162B GLN-269B HIS-89C ASP-108C ASN-109C VAL-159C GLY-160C GLN-269C |
| RdRp | LEU-270 PRO-323 THR-324 PHE-326 PHE-396 VAL-675 |
| ACE2-RBD | ILE-291 MET-366 ASP-367 LEU-370 THR-371 HIS-374 GLU-406 SER-409 LEU-410 PHE-438 GLN-442 1LE-446 |
| 3CLpro | THR-26 LEU-27 HIS-41 MET-49 TYR-54 PHE-140 LEU-141 ASN-142 CYS-145 HIS-164 MET-165 GLU-166 ASP-187 ARG-188 GLN-189 |
| NSP15 Active Site | HIS-235 GLY-248 HIS-250 LYS-290 CYS-291 VAL-292 SER-294 TRP-333 THR-341 TYR-343 PRO-344 LYS-345 LEU-346 |
| NSP15 Alternative Site | LYS-71 LYS-90 THR-167 THR-196 GLN-197 SER-198 ARG-199 ASN-200 LEU-252 ASP-273 SER-274 THR-275 LYS-277 TYR-279 VAL-295 ILE-296 ASP-297 |
| Spike | LEU-546A THR-547A ASP-568A THR-572A THR-573A PRO-589A MET-740B TYR-741B ILE-742B CYS-743B GLY-744B ASP-745B PHE-855B ASN-856B VAL-976B ASN-978B ARG-1000B |

Example 7

Figure 10:
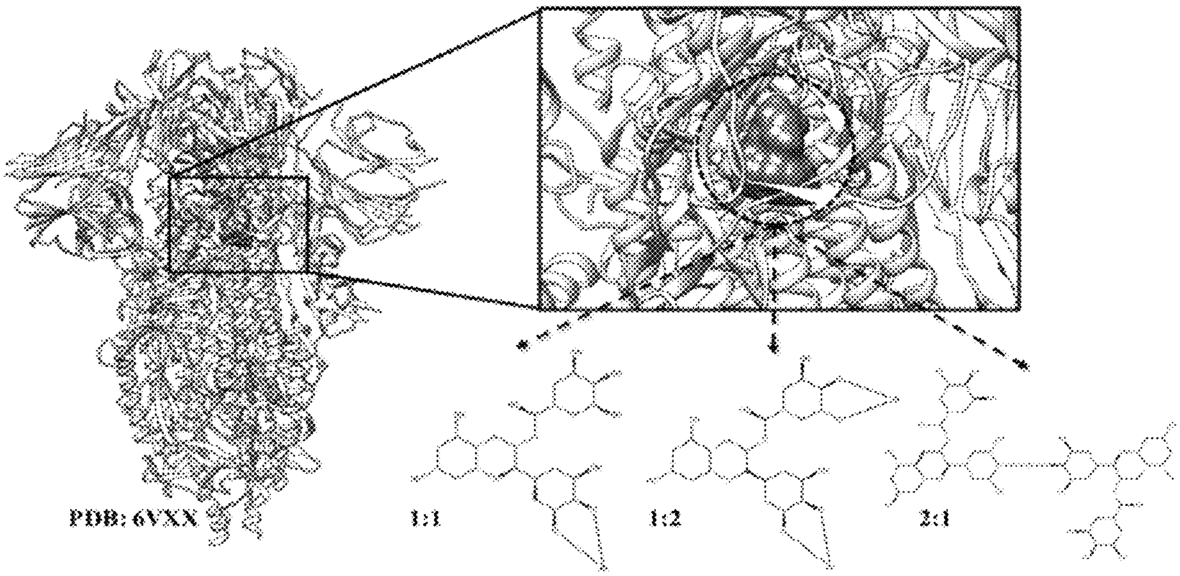
FIG. 10. SARS-CoV-2 Spike Protein (S) structure proposed as therapeutic target. The protein considered is S the, PDB code: 6VXX. The black circle refers to the interaction site with the three conformations of the EGCG-$Zn^{2+}$ complexes (1:1, 1:2 and 2:1 ratio).

EGCG-$Zn^{2+}$ Complexes Interact with Spike Protein of SARS-CoV-2 with More Favorable Energies than EGCG Molecule Alone or Zn Molecule Alone New molecular docking analyzes, using 3 conformations of EGCG-$Zn^{2+}$ complexes and the Spike Protein of SARS-CoV-2, indicate that the binding energy is favorable (FIG. 10). Considering the conformation of EGCG-$Zn^{2+}$ complexes 1:1 (1 EGCG: 1 $Zn^{2+}$), the binding energies obtained were −8.9 Kcal/mol. For the conformation of EGCG-$Zn^{2+}$ complexes 2:1 (2 EGCG: 1 $Zn^{2+}$), the binding energies obtained were −9.2 kcal/mol. For the conformation of EGCG-$Zn^{2+}$ complexes 1:2 (1 EGCG: 2 $Zn^{2+}$), the binding energies obtained were −8.4 Kcal/mol. Using the same methodology, for the EGCG molecule alone and zinc gluconate molecule alone, the binding energy obtained were −8.4 Kcal/mol and −6.2 Kcal/mol, respectively. The binding energies obtained reflect the in-silico feasibility of creating the Spike protein—EGCG-$Zn^{2+}$ complexes protein complex (Table 2), producing hydrophobic interactions, hydrogen bonds and salt bridges in the docking analysis. Table 3 shows the amino acids with which the ligands interact in each of the predicted pockets of each protein receptor. It should be noted that the docking analysis performed with the EGCG-$Zn^{2+}$ complexes present much more favorable energies than the analyzes performed only with EGCG molecule or Zn molecule alone; this allows us to infer that possibly the EGCG-$Zn^{2+}$ complexes will have a greater effect than EGCG, in-vivo.

Example 8

Figure 11:
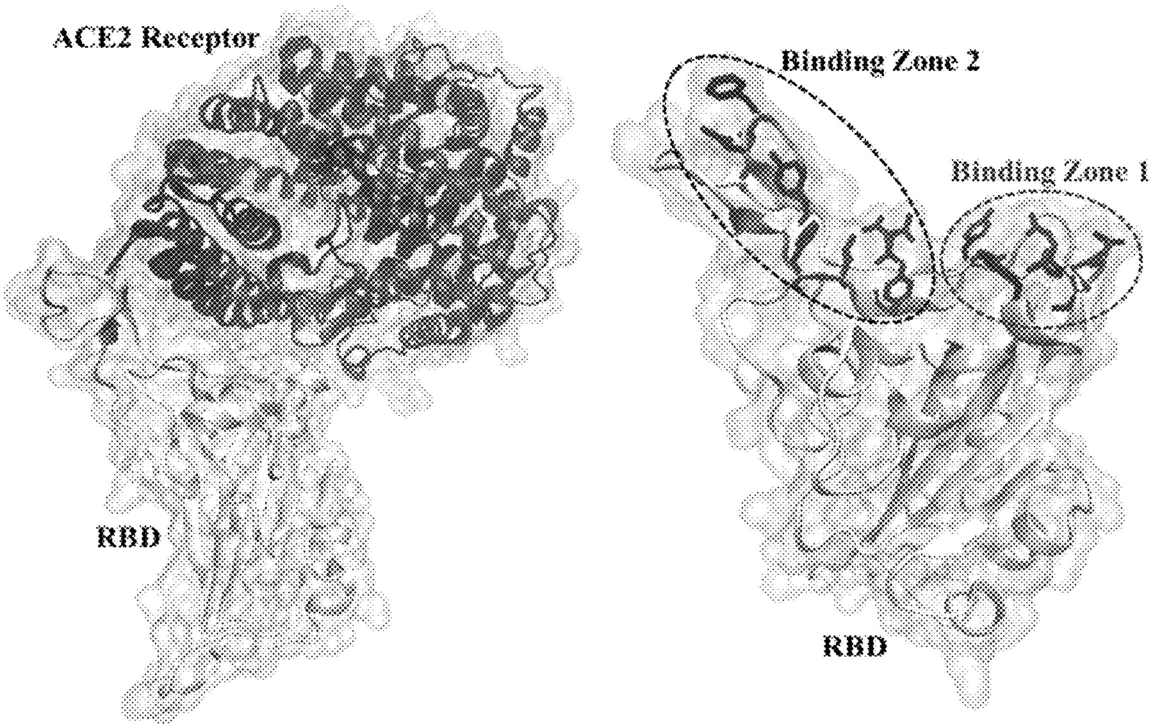
FIG. 11. RBD-ACE2 interaction proposed as therapeutic targets. The proteins complex considered are Angiotensin Converting Enzyme 2 receptor with Receptor Binding Domain of Spike protein, PDB code: 6M0J. The black circles refer to binding zones with the three conformations of the EGCG-$Zn^{2+}$ complexes (1:1, 1:2 and 2:1 ratio). The amino acid in binding zone 1 were: Gly496, Gln498, Gly502, Asn501, Thr500 and Tyr505 and amino acid in binding zone 2 were: Leu455, Tyr453, Tyr449, Gln493, Phe456, Tyr489, Asn487 and Phe486. Within the binding zones are located the lateral chains of amino acids of spike protein that participate in ACE2-RBD interaction.

EGCG-$Zn^{2+}$ Complexes Interact with RBD-ACE2 Binding Site with More Favorable Energies than EGCG Molecule Alone or Zn Molecule Alone A new molecular docking analysis was carried out, using as receptor protein only the structure of RBD (Receptor Binding Domain of Protein S, PDB: 6M0J, E chain). For this molecular docking analysis, the amino acids that interact with the ACE2 receptor in the first step of viral adsorption were identified, to focus the analysis on this area. The amino acids that interact in the ACE2-RBD complex are: Leu455, Tyr453, Tyr449, Gly496, Gln498, Gly502, Asn501, Thr500, Tyr505, Gln493, Phe456, Tyr489, Asn487 and Phe486. For this new docking, 2 possible binding zones were set where EGCG-$Zn^{2+}$ complexes could interact on the RBD domain. The zones were defined by proximity to the amino acids mentioned above, where for zone 1 the next amino acids are Gly496, Gln498, Gly502, Asn501, Thr500 and Tyr505; and for zone 2 they are Leu455, Tyr453, Tyr449, Gln493, Phe456, Tyr489, Asn487 and Phe486 (FIG. 11). The binding energies reported are as follows: for binding zone 1 with EGCG-$Zn^{2+}$ complexes 1:1 is −7.0 Kcal/mol, EGCG-$Zn^{2+}$ complexes 1:2 is −7.6 Kcal/mol, EGCG-$Zn^{2+}$ complexes 2:1 is −7.4 Kcal/mol; for binding zone 2 with EGCG-$Zn^{2+}$ complexes 1:1 is −5.6 Kcal/mol, EGCG-$Zn^{2+}$ complexes 1:2 is −5.7 Kcal/mol, EGCG-$Zn^{2+}$ complexes 2:1 is −6.3 Kcal/mol. In contrast, using the EGCG molecule alone and zinc gluconate alone, docked with RBD receptor in the binding zones, the binding energies were for binding zone 1 with the EGCG and zinc gluconate −6.9 Kcal/mol and −5.7 Kcal/mol, respectively. For the binding zone 2 with EGCG and zinc gluconate −5.4 Kcal/mol and −4.8 Kcal/mol, respectively. For this new analysis, it is concluded that binding zone 1 defined above has favorable energies in the formation of the RBD-EGCG-$Zn^{2+}$ complex (Table 4).

TABLE 4

Binding energies reported in the formation of EGCG-$Zn^{2+}$—RBD complexes

| | PDB | (EGCG-$Zn^{2+}$ Complex) (Kcal/mol) 1:1 | 2:1 | 1:2 | EGCG (Kcal/mol) | Zinc Gluconate |
|---|---|---|---|---|---|---|
| Binding Zone 1 | 6M0J_A | −7.0 | −7.4 | −7.6 | −6.9 | −5.7 |
| Binding Zone 2 | 6M0J_A | −5.6 | −6.3 | −5.7 | −5.4 | −4.8 |

Example 9

Figure 12A:
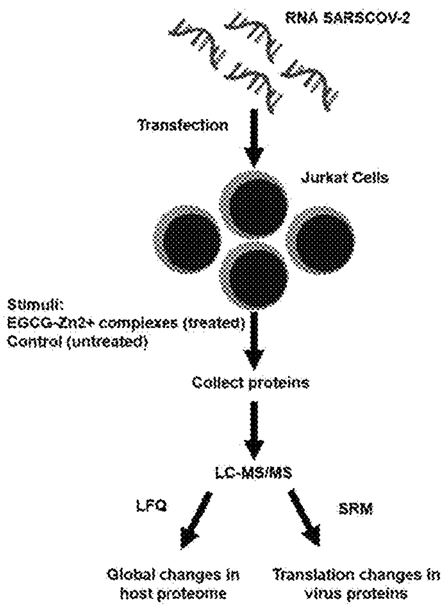
FIGS. 12A, 12B, and 12C. Global changes in protein expression in Jurkat cells transfected with viral RNA isolated from COVID-19 patients.
Figure 12B:
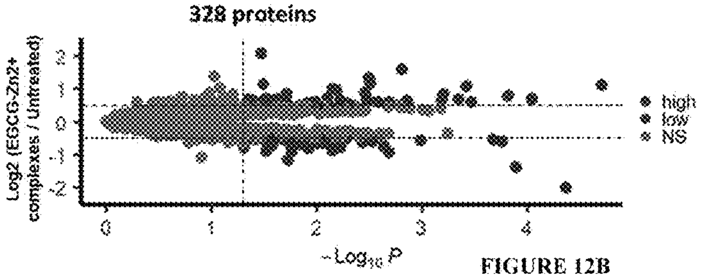
Figure 12C:
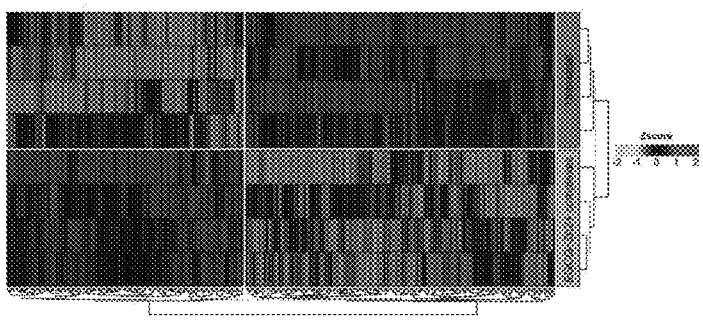

EGCG-$Zn^{2+}$ Complexes Generate Protein Expression Changes in Jurkat Cells Transfected with Viral RNA Isolated from COVID-19 Patients Jurkat cells ($2\times10^5$) were transfected with viral RNA isolated from COVID-19 patients (3 ng), cultivated in RPMI medium until reach a 90% confluence and incubated for 24h with EGCG-$Zn^{2+}$ (2μ/mL) complexes (Treated) or ST (Untreated). The cells pellet was washed twice with PBS1X and proteins were extracted and resuspended in 8 M Urea with 25 mM of ammonium bicarbonate pH 8. The proteins were quantified with Qubit protein assay, reduced with 20 mM DTT for one hour, alkylated with 20 mM Iodoacetamide in the dark for one hour, diluted ten times with 25 mM of ammonium bicarbonate pH 8 and digested with trypsin (1:50 ratio protease:protein) overnight at 37° C. Peptides were cleaned using C-18 Sep Pack using the protocol suggested by the manufacturer, the eluted peptides were dried using a rotary concentrator at 4° C., and resuspended with 0.1% v/v formic acid and quantified using Direct detect. We employed a nanoElute liquid chromatography system (Bruker Daltonics), peptides (200 ng of digest) were separated within 90 min at a flow rate of 400 nL/min on a reversed-phase column Aurora Series CSI (25 cm×75 μm i.d. C18 1.6 μm) (IonOpticks, Australia) with 50° C. Mobile phases A and B were water and acetonitrile with 0.1% v/v formic acid, respectively. The B % was linearly increased from 2 to 17% within 57 min, followed by an increase to 25% B within 21 min and further to 35% within 13 min, followed by a washing step at 85% B and re-equilibration. All samples were analyzed on a hybrid trapped ion mobility spectrometry (TIMS) quadrupole time-of-flight mass spectrometer (MS) (TIMS-TOF Pro, Bruker Daltonics) via a Captive Spray nano-electrospray ion source. The MS was operated in data-dependent mode for the ion mobility-enhanced spectral library generation. We set the accumulation and ramp time to 100 ms each and recorded mass spectra in the range from m/z 100-1700 in positive electrospray mode. The ion mobility was scanned from 0.6 to 1.6 Vs/$cm^2$. The overall acquisition cycle of 1.16 s comprised one full TIMS-MS scan and 10 parallel accumulation-serial fragmentation (PASEF) MS/MS scans. Tandem mass spectra were extracted by Tims Control version 2.0. Charge state deconvolution and deisotoping were not performed. All MS/MS samples were analyzed using MSFragger version 3.2. This was set up to search the *Homo sapiens* proteome (UP000005640, 77027 entries) assuming the digestion enzyme trypsin. The fragment ion mass tolerance was 0,050 Da and a parent ion tolerance of 20 ppm. Carbamidomethyl of cysteine was specified as a fixed modification. Deamidated of asparagine and glutamine, oxidation of methionine, acetyl of the n-terminus and carbamyl of lysine and the n-terminus as variable modifications. Ion quant output report were concatenated, and protein/peptide normalized intensity was the abundance parameter used to detect global changes in protein abundance induced by EGCG-$Zn^{2+}$ complexes on the host proteome, through quantitative analysis by Label Free Quantification comparing the groups of cells transfected with SARS CoV-2 RNA and treated with EGCG-$Zn^{2+}$ complexes (Treated) against ST (Untreated) cells. The enrichment analysis of biological pathways was carried out using the Cluster Profiler, consulting proteins with significant differential expression ($p<0.05$) against Reactome *Homo sapiens*. Only significant overrepresented pathways were highlighted ($p<0.01$) (FIG. 12A) We found 3216 quantifiable proteins where 328 significantly varied their abundance ($p<0.05$) in the EGCG-$Zn^{2+}$ complexes (Treated) and ST (Untreated) (FIG. 12B). Heatmap analysis in conjunction with the hierarchical grouping of the samples shows a clear effect of EGCG-$Zn^{2+}$ complexes on the abundance of several proteins, where a group of proteins tends to increase their expression levels when stimulated with EGCG-$Zn^{2+}$ complexes, and vice versa (FIG. 12C).

Example 10

Figure 13:
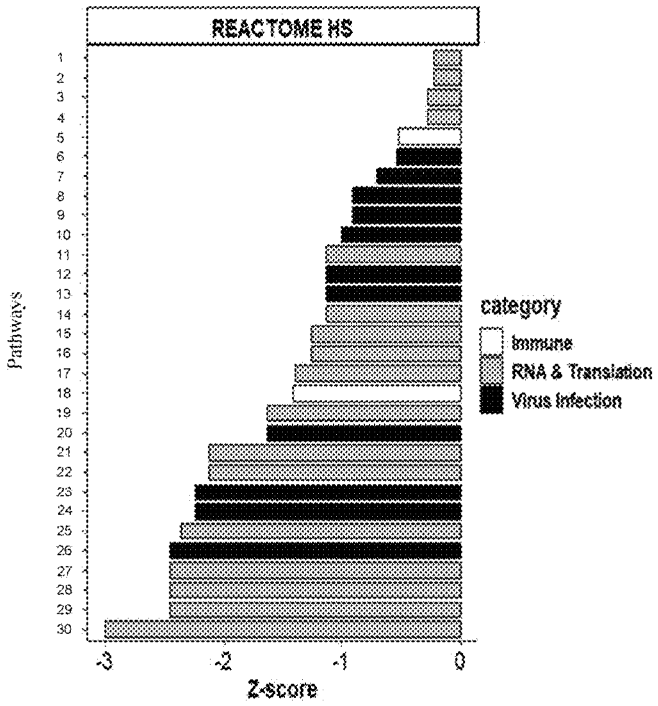
FIG. 13. Analysis of overrepresentation of SARS-CoV-2 proteins in Jurkat cells transfected with viral RNA isolated from COVID-19 patients. Pathway analysis of proteins showing significant differences ($p<0.05$) between groups of cells treated with EGCG-$Zn^{2+}$ complexes (Treated) and ST (Untreated). They were contrasted against the Reactome *Homo sapiens* database. The bar charts for each data repository indicate the activation level or z score of each pathway. The colors of the bars indicate the category to which the pathway belongs, such as Immune (white), RNA & Translation (gray) and Viral infection (black). The level of activation of a particular pathway is given by the z score, which gives us some clue as to whether the biological process is more likely to decrease (negative value) or increase (positive value). It is calculated as follows: z score=(up-down)/√count. Where up and down are the number of genes/proteins that were up-regulated (log FC>0) or down-regulated (log FC<0), respectively. And the count is the total of proteins/genes found for the pathway in question (up+down).

EGCG-$Zn^{2+}$ Complexes Reduce the Activity of Biological Processes Related to SARS CoV-2 Infection in the Host Proteome in Jurkat Cells Transfected with Viral RNA Isolated from COVID-19 Patients In order to investigate the effect that EGCG-$Zn^{2+}$ complexes induce on cellular processes in our model of transfection with viral RNA isolated from COVID-19 patients, an enrichment analysis of biological pathways was carried out using the Cluster Profiler app, consulting the 328 proteins with significant differential expression. ($p<0.05$) against Reactome *Homo sapiens* (FIG. 13). The number legends 1-30 along the y-axis in FIG. 13 refer to the following pathways: 1 refers to mRNA splicing—major pathway; 2 refers mRNA splicing; 3 refers to transcriptional regulation by small RNAs; 4 refers to gene silencing by RNA; 5 refers to neutrophil degranulation; 6 refers to host interactions of HIV factors; 7 refers to interactions of Rev with host cellular proteins; 8 refers to late phase of HIV life cycle; 9 refers to HIV life cycle; 10 refers to HIV infection; 11 refers to SUMOylation of RNA binding proteins; 12 refers to Rev—mediated nuclear export of HIV RNA; 13 refers to nuclear import of Rev protein; 14 refers to mRNA splicing—minor pathway; 15 refers to snRNP assembly; 16 refers to metabolism of non-coding RNA; 17 refers to processing of capped Intron-containing Pre-mRNA; 18 refers to regulation of HSF1-mediated heat shock response; 19 refers to NEP/NS2 interacts with the cellular export machinery; 20 refers to export of viral ribonucleoproteins from nucleus; 21 refers to tRNA processing in the nucleus; 22 refers to transport of mature transcript to cytoplasm; 23 refers to Vpr-mediated nuclea import PICs; 24 refers to transport of ribonucleoproteins into the host nucleus; 25 refers to SUMOylation; 26 refers to viral messenger RNA synthesis; 27 refers to transport of the SLBP dependant mature mRNA; 28 refers to transport of mature mRNAs derived from intronless transcripts; 29 refers to SUMOylation of ubiquitinylation proteins; and 30 refers to SUMOylation of DNA replication proteins.

It was revealed that the processes where these proteins participate were significantly overrepresented ($p<0.01$). We found enriched processes associated with Viral Infection such as "Viral Messenger RNA Synthesis", "HIV Infection", "Late Phase of HIV Life Cycle," Interactions of Rev with host cellular proteins", which accounts for the entry of RNA SARS CoV-2 to the cell. Furthermore, we found crucial biological processes for viral amplification associated with RNA & Translation such as "Processing of Capped Intron-Containing Pre-mRNA", "mRNA Splicing", "Transport of Mature Transcript to Cytoplasm" and "tRNA processing in the nucleus". This is consistent with what has been demonstrated in a model of Caco-2 cells infected with SARS CoV-2, where these processes are significantly altered (Bojkova et al. Proteomics of SARS CoV-2-infected host cells reveals therapy targets. Nature 583.7816 (2020): 469-472.) Other significantly decreased processes were "Neutrophil degranulation", "Regulation of HSF1-mediated heat shock response" were found downregulated in EGCG-$Zn^{2+}$ complexes (Treated) vs ST (Untreated), processes key in inflammatory response during SARS CoV-2 infection. An extensive pathway analysis by ClusterProfiler app ($p<0.01$) in through consultation with other pathway repositories such as GO-BP and KEGG (Table 5). Like the Reactome analysis, all these pathways are significantly enriched ($p<0.01$) in EGCG-$Zn^{2+}$ complexes treated cells. This reflects that the expression changes in our experiment are characteristic of "infected" cells, such as protein translation, viral infection, and cellular immunity. Which are decreased in cells transfected with viral RNA isolated from COVID-19 patients and treated with EGCG-$Zn^{2+}$ complexes. We hypothesize that under our viral RNA transfection model, EGCG-$Zn^{2+}$ complexes induce in the host a down-regulation of key processes for the infection and replication of SARS CoV-2, as well as an anti-inflammatory effect thought modulating the activity of pathways of cellular immunity. This effect is complemented by the inhibition of the replication of viral proteins such as spike protein, presumably through the interaction of the formulation with these proteins.

TABLE 5

Pathways differed in EGCG-$Zn^{2+}$ complexes vs Untreated

| Pathway name | Category | Gene set | p-value | Pathway source |
|---|---|---|---|---|
| Regulation of expression of SLITs and ROBOs | Immune | 23 | 1.75.E−09 | Reactome |
| Signaling by ROBO receptors | Immune | 23 | 1.09.E−07 | Reactome |
| Neutrophil degranulation | Immune | 33 | 1.82.E−06 | Reactome |
| HSF1 activation | Immune | 4 | 1.80.E−03 | Reactome |
| Interleukin-1 family signaling | Immune | 4 | 1.45.E−03 | Reactome |
| Regulation of HSF1-mediated heat shock response | Immune | 8 | 2.76.E−03 | Reactome |
| IL-17 signaling pathway | Immune | 2 | 6.21.E−03 | KEGG |
| Antigen processing and presentation | Immune | 2 | 1.76.E−02 | KEGG |
| HIF-1 signaling pathway | Immune | 5 | 1.96.E−02 | KEGG |

TABLE 5-continued

Pathways differed in EGCG-$Zn^{2+}$ complexes vs Untreated

| Pathway name | Category | Gene set | p-value | Pathway source |
|---|---|---|---|---|
| IL-17 signaling pathway | Immune | 2 | 6.21.E−03 | KEGG |
| Antigen processing and presentation | Immune | 2 | 1.76.E−03 | KEGG |
| FoxO signaling pathway | Immune | 3 | 1.36.E−03 | KEGG |
| Fc epsilon RI signaling pathway | Immune | 1 | 1.80.E−03 | KEGG |
| B cell receptor signaling pathway | Immune | 1 | 2.37.E−03 | KEGG |
| Fc gamma R-mediated phagocytosis | Immune | 3 | 3.16.E−03 | KEGG |
| T cell receptor signaling pathway | Immune | 1 | 3.98.E−03 | KEGG |
| HIF-1 signaling pathway | Immune | 5 | 1.96.E−02 | KEGG |
| neutrophil mediated immunity | Immune | 33 | 5.34.E−09 | GO-BP |
| neutrophil degranulation | Immune | 32 | 1.08.E−08 | GO-BP |
| neutrophil activation involved in immune response | Immune | 32 | 1.19.E−08 | GO-BP |
| neutrophil activation | Immune | 32 | 1.88.E−08 | GO-BP |
| RNA splicing | RNA & Translation | 29 | 2.79.E−07 | GO-BP |
| SRP-dependent cotranslational protein targeting to membrane | RNA & Translation | 21 | 4.98.E−11 | Reactome |
| Eukaryotic Translation Elongation | RNA & Translation | 19 | 1.13.E−10 | Reactome |
| rRNA processing | RNA & Translation | 26 | 3.93.E−10 | Reactome |
| Nonsense-Mediated Decay (NMD) | RNA & Translation | 19 | 2.27.E−09 | Reactome |
| rRNA processing in the nucleus and cytosol | RNA & Translation | 24 | 3.35.E−09 | Reactome |
| Selenocysteine synthesis | RNA & Translation | 17 | 3.89.E−09 | Reactome |
| Eukaryotic Translation Termination | RNA & Translation | 17 | 3.89.E−09 | Reactome |
| Major pathway of rRNA processing in the nucleolus and cytosol | RNA & Translation | 23 | 5.76.E−09 | Reactome |
| Formation of a pool of free 40 S subunits | RNA & Translation | 17 | 1.34.E−08 | Reactome |
| Processing of Capped Intron-Containing Pre-mRNA | RNA & Translation | 25 | 4.81.E−08 | Reactome |
| GTP hydrolysis and joining of the 60 S ribosomal subunit | RNA & Translation | 17 | 5.81.E−08 | Reactome |
| Translation | RNA & Translation | 27 | 7.98.E−08 | Reactome |
| Selenoamino acid metabolism | RNA & Translation | 17 | 1.17.E−07 | Reactome |
| Eukaryotic Translation Initiation | RNA & Translation | 17 | 1.23.E−07 | Reactome |
| Cap-dependent Translation Initiation | RNA & Translation | 17 | 1.23.E−07 | Reactome |
| mRNA Splicing-Major Pathway | RNA & Translation | 19 | 2.78.E−06 | Reactome |
| mRNA Splicing | RNA & Translation | 19 | 5.14.E−06 | Reactome |
| snRNP Assembly | RNA & Translation | 10 | 1.06.E−05 | Reactome |
| Metabolism of non-coding RNA | RNA & Translation | 10 | 1.06.E−05 | Reactome |
| SUMOylation | RNA & Translation | 18 | 1.57.E−05 | Reactome |
| SUMOylation of DNA replication proteins | RNA & Translation | 9 | 2.27.E−05 | Reactome |
| Transcriptional regulation by small RNAs | RNA & Translation | 13 | 3.43.E−05 | Reactome |
| Regulation of mRNA stability by proteins that bind AU-rich elements | RNA & Translation | 11 | 1.65.E−04 | Reactome |
| Gene Silencing by RNA | RNA & Translation | 13 | 4.37.E−04 | Reactome |
| Formation of the ternary complex, and subsequently, the 43 S complex | RNA & Translation | 8 | 4.52.E−04 | Reactome |
| tRNA processing | RNA & | 8 | 9.44.E−04 | Reactome |

TABLE 5-continued

Pathways differed in EGCG-$Zn^{2+}$ complexes vs Untreated

| Pathway name | Category | Gene set | p-value | Pathway source |
|---|---|---|---|---|
| in the nucleus | Translation | | | |
| Translation initiation complex formation | RNA & Translation | 8 | 1.02.E−03 | Reactome |
| Ribosomal scanning and start codon recognition | RNA & Translation | 8 | 1.02.E−03 | Reactome |
| Activation of the mRNA upon binding of the cap-binding complex and eIFs, and subsequent binding to 43 S | RNA & Translation | 8 | 1.14.E−03 | Reactome |
| NEP/NS2 Interacts with the Cellular Export Machinery | RNA & Translation | 6 | 1.15.E−03 | Reactome |
| SUMOylation of RNA binding proteins | RNA & Translation | 7 | 1.62.E−03 | Reactome |
| RHO GTPase Effectors | RNA & Translation | 20 | 1.80.E−03 | Reactome |
| Transport of the SLBP Dependant Mature mRNA | RNA & Translation | 6 | 2.08.E−03 | Reactome |
| mRNA Splicing-Minor Pathway | RNA & Translation | 7 | 2.70.E−03 | Reactome |
| SUMOylation of ubiquitinylation proteins | RNA & Translation | 6 | 2.92.E−03 | Reactome |
| Transport of Mature mRNAs Derived from Intronless Transcripts | RNA & Translation | 6 | 4.82.E−03 | Reactome |
| Metabolism of amino acids and derivatives | RNA & Translation | 20 | 7.04.E−03 | Reactome |
| Transport of Mature Transcript to Cytoplasm | RNA & Translation | 8 | 8.15.E−03 | Reactome |
| Ribosome | RNA & Translation | 18 | 1.90.E−23 | KEGG |
| Spliceosome | RNA & Translation | 15 | 3.11.E−12 | KEGG |
| RNA transport | RNA & Translation | 15 | 3.03.E−07 | KEGG |
| Proteasome | RNA & Translation | 3 | 1.06.E−06 | KEGG |
| Protein processing in endoplasmic reticulum | RNA & Translation | 10 | 4.37.E−04 | KEGG |
| RNA degradation | RNA & Translation | 4 | 1.93.E−03 | KEGG |
| mRNA catabolic process | RNA & Translation | 37 | 4.81.E−15 | GO-BP |
| cotranslational protein targeting to membrane | RNA & Translation | 20 | 1.28.E−12 | GO-BP |
| establishment of protein localization to endoplasmic reticulum | RNA & Translation | 20 | 6.92.E−12 | GO-BP |
| translational initiation | RNA & Translation | 21 | 3.47.E−09 | GO-BP |
| RNA splicing, via transesterification reactions | RNA & Translation | 26 | 2.79.E−07 | GO-BP |
| protein folding | RNA & Translation | 20 | 2.79.E−07 | GO-BP |
| ribosome biogenesis | RNA & Translation | 22 | 9.55.E−07 | GO-BP |
| regulation of mRNA stability | RNA & Translation | 17 | 1.08.E−06 | GO-BP |
| ribonucleoprotein complex assembly | RNA & Translation | 21 | 1.30.E−06 | GO-BP |
| RNA localization | RNA & Translation | 19 | 1.55.E−06 | GO-BP |
| ribonucleoprotein complex subunit organization | RNA & Translation | 21 | 2.60.E−06 | GO-BP |
| nucleic acid transport | RNA & Translation | 16 | 1.25.E−05 | GO-BP |
| RNA transport | RNA & Translation | 16 | 1.25.E−05 | GO-BP |
| ncRNA export from nucleus | RNA & Translation | 8 | 1.25.E−05 | GO-BP |
| nucleocytoplasmic transport | RNA & Translation | 21 | 2.16.E−05 | GO-BP |
| ribonucleoprotein complex localization | RNA & Translation | 12 | 6.31.E−05 | GO-BP |

TABLE 5-continued

Pathways differed in EGCG-$Zn^{2+}$ complexes vs Untreated

| Pathway name | Category | Gene set | p-value | Pathway source |
|---|---|---|---|---|
| nucleus organization | RNA & Translation | 10 | 1.48.E−03 | GO-BP |
| Ribosome | RNA & Translation | 18 | 1.90.E−23 | KEGG |
| Spliceosome | RNA & Translation | 15 | 3.11.E−12 | KEGG |
| RNA transport | RNA & Translation | 15 | 3.03.E−07 | KEGG |
| Proteasome | RNA & Translation | 3 | 1.06.E−06 | KEGG |
| Protein processing in endoplasmic reticulum | RNA & Translation | 10 | 4.37.E−04 | KEGG |
| RNA degradation | RNA & Translation | 4 | 1.93.E−03 | KEGG |
| Influenza Life Cycle | Virus Infection | 25 | 5.30.E−12 | Reactome |
| Influenza Viral RNA Transcription and Replication | Virus Infection | 24 | 5.30.E−12 | Reactome |
| Influenza Infection | Virus Infection | 25 | 1.21.E−11 | Reactome |
| Infectious disease | Virus Infection | 36 | 3.39.E−10 | Reactome |
| Peptide chain elongation | Virus Infection | 18 | 3.48.E−10 | Reactome |
| Viral mRNA Translation | Virus Infection | 18 | 3.48.E−10 | Reactome |
| Interactions of Rev with host cellular proteins | Virus Infection | 8 | 3.72.E−05 | Reactome |
| Host Interactions of HIV factors | Virus Infection | 14 | 5.74.E−05 | Reactome |
| Nuclear import of Rev protein | Virus Infection | 7 | 2.03.E−04 | Reactome |
| Rev-mediated nuclear export of HIV RNA | Virus Infection | 7 | 2.40.E−04 | Reactome |
| Export of Viral Ribonucleoproteins from Nucleus | Virus Infection | 6 | 1.61.E−03 | Reactome |
| HIV Infection | Virus Infection | 16 | 2.15.E−03 | Reactome |
| Viral Messenger RNA Synthesis | Virus Infection | 6 | 5.29.E−03 | Reactome |
| Late Phase of HIV Life Cycle | Virus Infection | 11 | 5.39.E−03 | Reactome |
| Transport of Ribonucleoproteins into the Host Nucleus | Virus Infection | 5 | 7.21.E−03 | Reactome |
| Vpr-mediated nuclear import of PICs | Virus Infection | 5 | 9.06.E−03 | Reactome |
| HIV Life Cycle | Virus Infection | 11 | 9.78.E−03 | Reactome |
| Viral carcinogenesis | Virus Infection | 10 | 1.87.E−06 | KEGG |
| Epstein-Barr virus infection | Virus Infection | 6 | 1.56.E−05 | KEGG |
| Hepatitis C | Virus Infection | 6 | 1.57.E−04 | KEGG |
| Hepatitis B | Virus Infection | 7 | 1.88.E−04 | KEGG |
| Viral myocarditis | Virus Infection | 2 | 1.36.E−03 | KEGG |
| Measles | Virus Infection | 3 | 2.73.E−02 | KEGG |
| Influenza A | Virus Infection | 5 | 3.93.E−02 | KEGG |
| Kaposi sarcoma-associated herpesvirus infection | Virus Infection | 4 | 4.44.E−02 | KEGG |
| viral transcription | Virus Infection | 25 | 3.42.E−13 | GO-BP |
| viral gene expression | Virus Infection | 25 | 1.28.E−12 | GO-BP |
| viral life cycle | Virus Infection | 17 | 9.96.E−04 | GO-BP |
| intracellular transport of virus | Virus Infection | 7 | 9.96.E−04 | GO-BP |

TABLE 5-continued

Pathways differed in EGCG-$Zn^{2+}$ complexes vs Untreated

| Pathway name | Category | Gene set | p-value | Pathway source |
|---|---|---|---|---|
| Viral carcinogenesis | Virus Infection | 10 | 1.87.E−06 | KEGG |
| Epstein-Barr virus infection | Virus Infection | 6 | 1.56.E−05 | KEGG |
| Hepatitis C | Virus Infection | 6 | 1.57.E−04 | KEGG |
| Hepatitis B | Virus Infection | 7 | 1.88.E−04 | KEGG |
| Viral myocarditis | Virus Infection | 2 | 1.36.E−03 | KEGG |
| Measles | Virus Infection | 3 | 2.73.E−02 | KEGG |
| Influenza A | Virus Infection | 5 | 3.93.E−02 | KEGG |
| Kaposi sarcoma-associated herpesvirus infection | Virus Infection | 4 | 4.44.E−02 | KEGG |

Example 11

EGCG-$Zn^{2+}$ Complexes Block the Translation of SARS COV-2 Spike Protein in Jurkat Cells Transfected with Viral RNA Isolated from COVID-19 Patients We investigated how EGCG-$Zn^{2+}$ complexes affected the translation of Spike Protein, which is the largest protein in SARS CoV-2, and key in the host entry process. The specific peptide of Spike Protein with the sequence GVYYPDK was detected and standardized from nasal swabs positive for SARS CoV-2. All samples were analyzed on a hybrid trapped ion mobility spectrometry (TIMS) quadrupole time-of-flight mass spectrometer (MS) (TIMS-TOF Pro, Bruker Daltonics) via a Captive Spray nano-electrospray ion source. Single Reaction Monitoring (SRM) method was designed in Skyline software platform and samples were analyzed in SRM capture mode of our mass spectrometer, measuring specific peptide precursors belonging to Spike Protein. The SRM assay was designed as follows: samples of nasopharyngeal swabs from positive SARS CoV-2 patients (validated by PCR) were selected and analyzed. Through deep proteomics strategy peptide spectral libraries were generated, and peptides with high reproducibility, accuracy and sensitivity were selected using the Skyline platform (MacCoss Lab). For quantification, the best peptides were synthesized and marked by adding C13 and N15 in their Lys and Arg residues (heavy peptides). The specific peptide GVYYPDK had the best performance and reproducibility foe quantification. The absolute quantification of peptides in samples was determined by interpolating the abundance (intensity) of the peptides with a calibration curve made with heavy peptides.

Figure 14A:
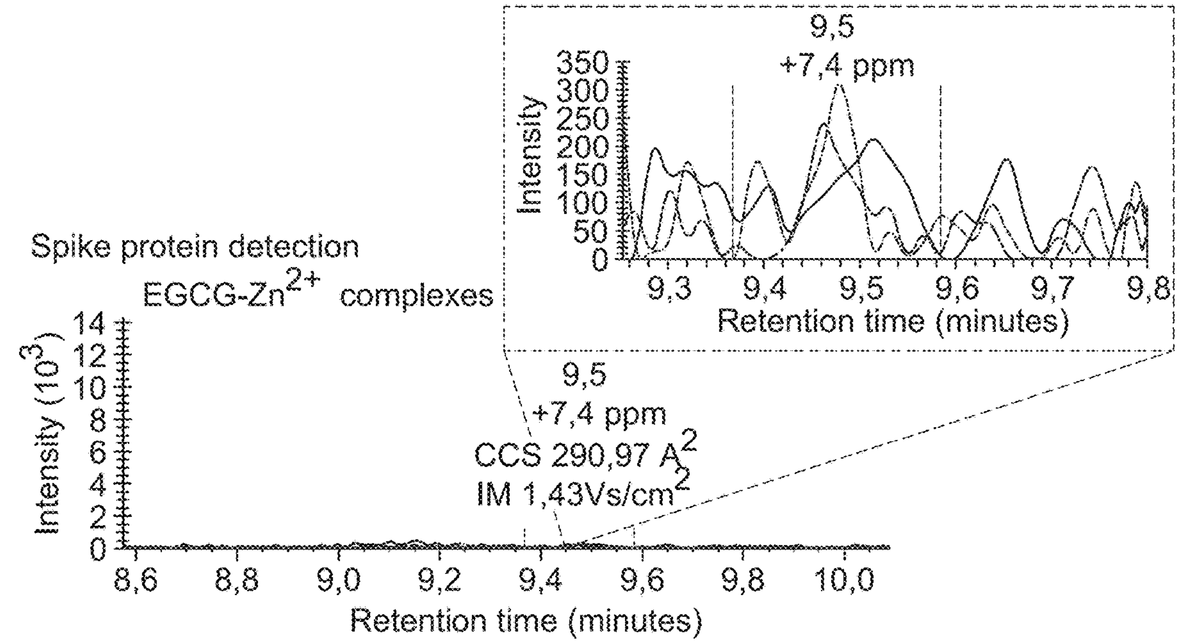
FIGS. 14A and 14B. Detection and quantification of SARS-CoV-2 proteins in Jurkat cells transfected with viral RNA isolated from COVID-19 patients. Targeted proteomics. The same samples previously used in the LFQ approach were analyzed by targeted proteomics, which is a detection method that allows one or a group of specific proteins to be followed within a complex mixture, through the screening of a specific peptide. The abundance parameter is the intensity of the measured peptide.
Figure 14B:
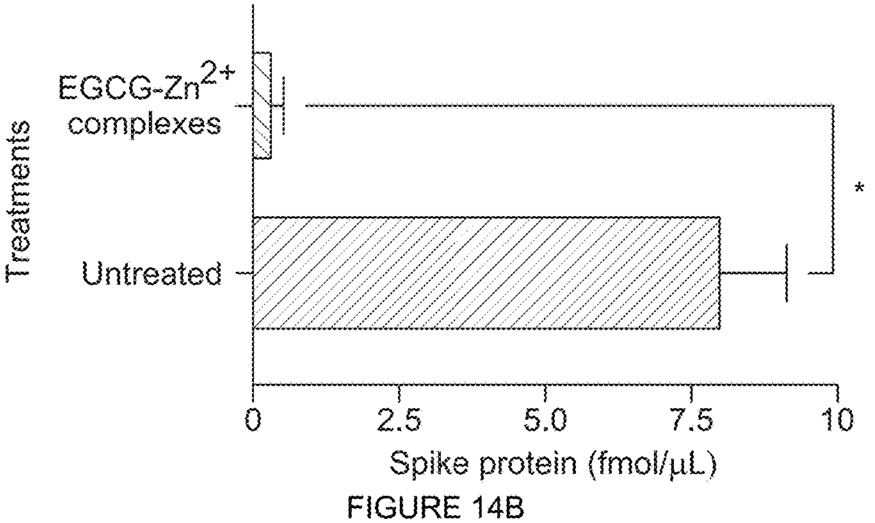

Thus, through our SRM method, we measure the expression of SARS CoV-2 spike protein in protein extract of Jurkat cells transfected with SARS COV2 RNA (3 ng) and incubated with EGCG-$Zn^{2+}$ complexes (Treated) and untreated transfected controls ST (Untreated). SRM confirmed that in Jurkat cells transfected with viral RNA isolated from COVID-19 patients and treated with EGCG-$Zn^{2+}$ complexes exhibited an expression of Spike Protein significantly downregulated (over 99%, exceptionally low levels in the order of attomoles) compared to untreated transfected control (8 fmol/μl) (FIGS. 14A and 14B).

Example 12

Evaluation of Cytotoxicity of EGCG-$Zn^{2+}$ Complexes

Figure 16:
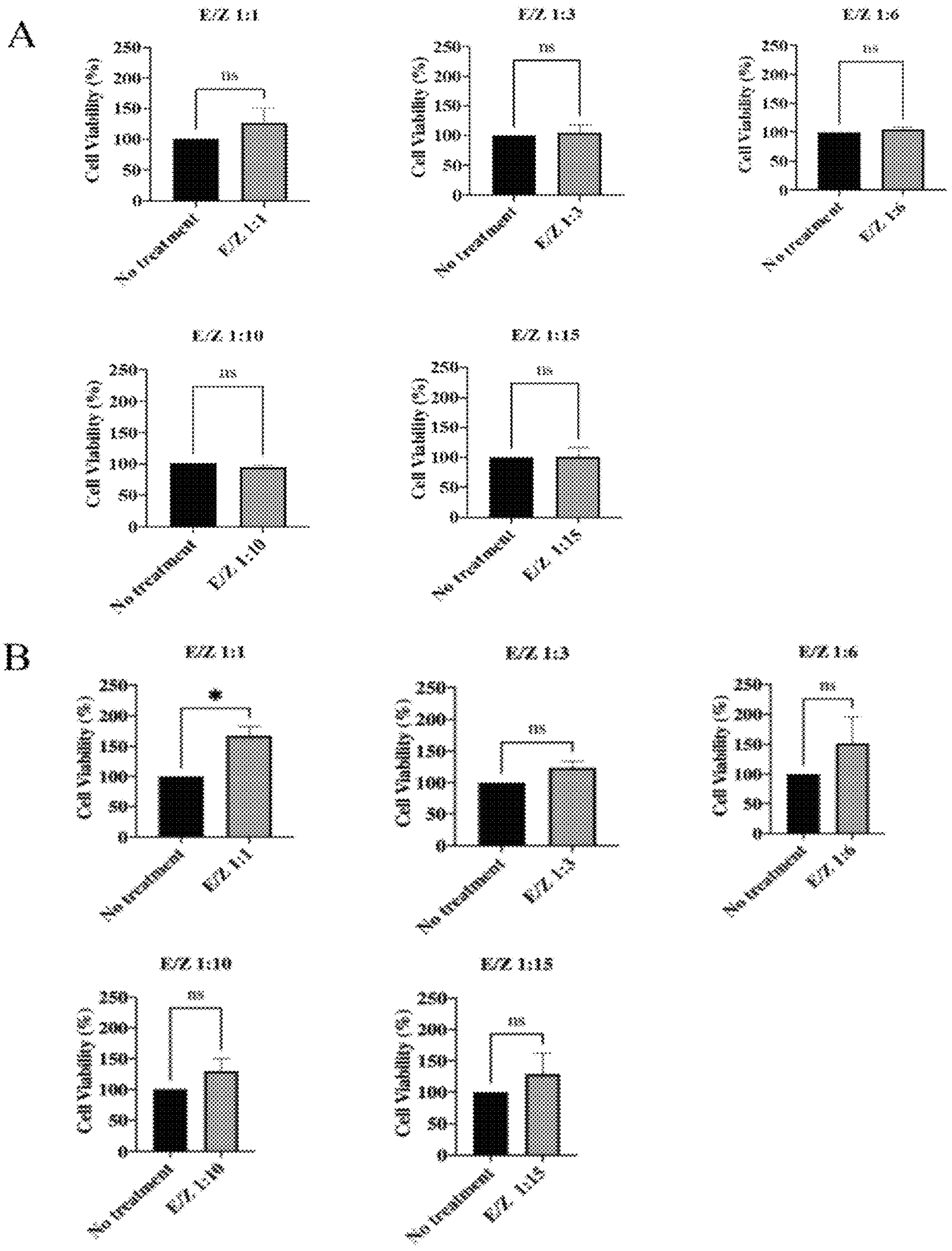
FIG. 16. Cytotoxicity assay in PBMCs (A) and Jurkat (B) using different proportions of $Zn^{2+}$. The viability of peripheral blood mononuclear cells was evaluated at different EGCG-$Zn^{2+}$ proportions (1:1, 1:3, 1:6, 1:10, 1:15) for 24 hours. For PBMCs, 6 ml is extracted of peripheral blood was extracted by puncture from human donors, using EDTA as anticoagulant, where the PBMC cells were collected using density gradients of percoll, subsequently the cells were synchronized in a culture in RPMI 1640 medium supplemented with 10% fetal bovine serum and the incorporation of IL2, for 24 h then the cells were washed and 100,000 cells were added per well in a 96-well plate, each well was treated with different proportions of EGCG-$Zn^{2+}$ (E:Z) in triplicate and maintained for 24 h at 37° C. and 5% CO2. The percentage of cell viability was measured using the Vybrant MTT Cell Proliferation Assay kit reagent. This assay measures the metabolic activity of cells.
Figure 17:
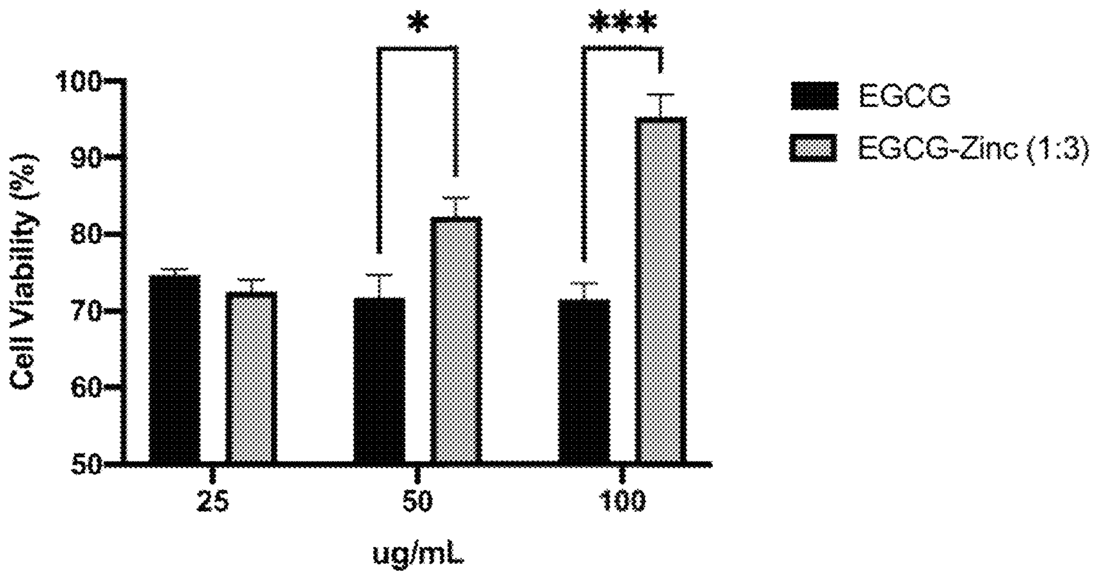
FIG. 17. Effect of EGCG-$Zn^{2+}$ on the viability of PBMCs. The viability of peripheral blood monocytic cells treated with different proportions of EGCG-$Zn^{2+}$ for 24 h was determined. The percentage of cell viability was measured using the Vybrant MTT Cell Proliferation Assay kit reagent.

The cytotoxicity of EGCG-$Zn^{2+}$ complexes were evaluated in human cell lines at a physiological pH (i.e. pH=7.4). For this, 100,000 Jurkat cells (human T lymphocytes) were treated with different concentrations of EGCG-$Zn^{2+}$ complexes (from 100 ug/ml to 1 ug/ml), for 24 h at 37° C. with 5% CO2. After the incubation time, the percentage of cell viability was measured using the Vybrant MTT Cell Proliferation Assay kit. This assay measures the metabolic activity of cells by reducing a soluble tetrazolium salt (MTT) to the form of insoluble formazan crystals. These viable cells contain NAD (P) H-dependent oxidoreductase enzymes that reduce MTT to formazan. Crystal formation can be measured at 570 nm using a spectrophotometer. The higher the value obtained, the greater the number of viable and metabolically active cells. After treating Jurkat cells with the different concentrations of EGCG-$Zn^{2+}$, the results show a dose response curve, whereas if the concentration of EGCG-$Zn^{2+}$ increases, the viability of the cells decreases. When comparing the toxicity curves of EGCG-$Zn^{2+}$ (1:3) versus EGCG, the curve of the former looks slightly favorable (FIG. 15). Considering that EGCG-$Zn^{2+}$ only has 2% of $Zn^{2+}$, it is agreed to carry out tests varying the concentrations of EGCG-$Zn^{2+}$. Assays were conducted using physiological concentrations of EGCG-$Zn^{2+}$ complexes. The composition of EGCG-$Zn^{2+}$ complex contains 250 mg of EGCG and 5 mg of $Zn^{2+}$, once absorbed in the body the proportions of these two changes, finding at least three times more $Zn^{2+}$ than EGCG in the blood. Considering this, the viability of Jurkat and PBMC immune cells was determined when treated with different proportions of EGCG-$Zn^{2+}$ (1:1, 1:3, 1:6, 1:10, 1:15). 100,000 cells were cultured per well which were treated with different proportions of EGCG-$Zn^{2+}$ and cultured for 24 h at 37° C. and 5% CO2. Through MTT assays, the percentage of viability of the treated cells was determined. The results showed that in primary PBMC cell lines, when treated with EGCG-$Zn^{2+}$ in 1:1 proportion, an activation of these cells was observed in comparison with the untreated ones. Which suggests that this formulation would not be toxic to immune cells and would also be increasing their metabolism and/or their proliferation. On the other hand, in the cells treated with the different EGCG-$Zn^{2+}$ formulations (1:3, 1:6, 1:10 and 1:15), a significant difference was not observed when the percentages of viability were compared with the untreated ones (FIG. 16A). This result indicates that increasing the proportions of $Zn^{2+}$ in the formulation would not be generating toxicity in immune cells. A similar result was obtained when the experiment was performed on the Jurkat (FIG. 16B) cell line. The cells treated with the different EGCG-$Zn^{2+}$ formulations did not show significant differences in the percentages of viability when they were compared with untreated cells. The effect of EGCG-$Zn^{2+}$ on the viability of peripheral blood lymphocyte cells (PBMC) was determined at different concentrations during 24 h. The results showed a decrease in viability in the cells when they were only treated with EGCG alone. On the other hand, when they were treated with EGCG-$Zn^{2+}$ in 1:3 proportions, an increase in the percentage of cell viability was observed, which suggests that the EGCG-$Zn^{2+}$ formulation is not only not toxic for this cell type, but which generates a protective effect, which is observed with the increase in cell viability (FIG. 17)

Example 13

Pharmacokinetics Parameters of EGCG-$Zn^{2+}$ in Human Serum

A fasting oral dose was applied using a capsule format containing 250 mg of EGCG and 5 mg of Zinc gluconate; serum samples were taken at different times (0; 15; 30; 60; 90; 120; 180 min). Extraction of serum samples were performed by mixing 200 µL serum with 20 µL 1 mM EDTA/2% v/v acetic acid/10% acetonitrile/1.5 ascorbic acid, 20 µL 55 mM ascorbic acid/3 mM EDTA and 20 µL 1.5 mM sodium acetate (pH 4.8). The samples were then thoroughly mixed with a vortex. For deconjugation of sulfates and glucuronides, 80 IA of BGTURBO® Glycerol Free High (Kura Biotech), 80 µL Instant Buffer I and 80 µL ultra-pure water, was added and the mixture, mixed and heated at 55° C. for 10 minutes. After incubation, 20 µL of 10 mM ascorbic acid (aqueous) and 10 µL of 2M hydrochloric acid were added. To achieve deproteinization, 1.8 mL of chilled (−20° C.) methanol was added and the mixture was refrigerated for 10 minutes at approx. 4° C. The samples were centrifuged, and the supernatant was transferred to glass tubes containing 20 IA of 10 mM ascorbic acid solution. The supernatant was evaporated to dryness in a centrifugal evaporator at 4° C. Once dry, the samples were reconstituted in 100 µL of 20 µL 1 mM EDTA/2% v/v acetic acid/10% acetonitrile/1.5 ascorbic acid and transferred to glass vials for autosamplers.

Figure 18:
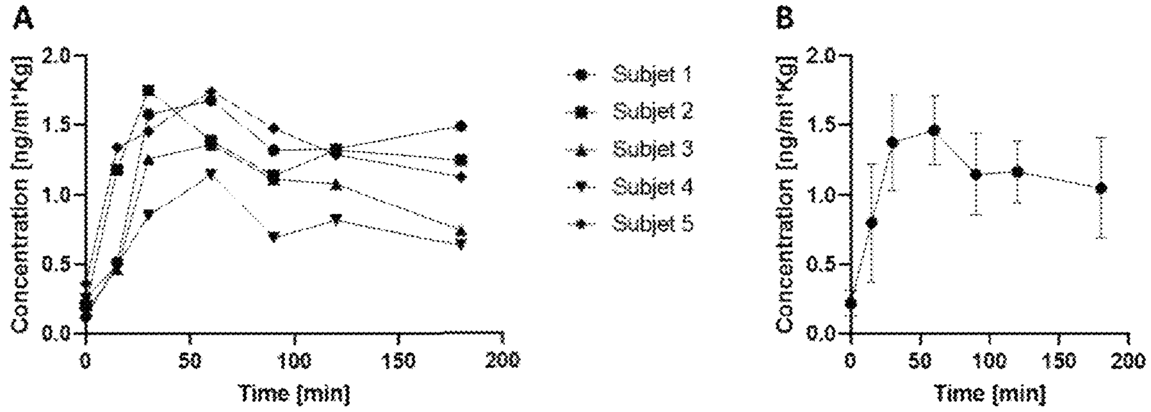
FIG. 18. Serum EGCG-$Zn^{2+}$ pharmacokinetics in humans (A) for each of the participants for EGCG-$Zn^{2+}$ formulation (250 mg EGCG and 5 mg Zinc Gluconate); Serum concentration was measured by UPLC-MS/MS in reverse phase C18. The curves were plotted in Graphpad 9.0. (B) Mean Curve with Standard error, from these graphs the values of Cmax, AUC, and Tmax were computed (see Table 6).

The EGCG in samples was measured by UPLC-MS/MS on the Elute UPLC system coupled to a Compact mass spectrometer (Bruker Daltonics, Germany). Instrument control and data collection were accomplished using oTOF software. Separation was achieved using a 1.7 µm particle, 2.1×100 mm Kinetex C18 column with Guard Column "Security guard Ultra". A binary solvent gradient was used using 0.1% aqueous formic acid (A) and 0.1% formic acid in Acetonitrile (B) as mobile phases. The solvents were programmed consecutively as follows; an isocratic composition of 5% B for 2 minutes, a linear gradient of 5-10% B from 2 to 8 min, a linear gradient of 10-95% B for 11 to 15 min, (total run time of 15 min). The injection volume was 4 µL. The column temperature was maintained at 35° C. and a flow rate of 0.5 ml/min was used. Electrospray ionization was set up in negative ion mode using the following settings: source temperature 250° C., conical gas flow 9 L/min, capillary voltage 4.5 kV. The mass spectrometer was set to auto MS/MS mode. Peak area integration and data processing were done using the Skyline environment (MacCoss Lab). The concentration of EGCG in sample was determined through interpolation of peak area on the samples with calibration curve of EGCG standard (324880, Sigma-Aldrich) where concentrations used was 2, 20, 50, 100, 500, 1000, 1500 and 2000 ng/mL. Later the data were plotted in corrected concentration (ng/ml*Kg) v/s Time (min) as shown in FIGS. 18A and 18B, observing that the maximum concentration in all the individuals is similar with a low variation between them, which shows that EGCG-$Zn^{2+}$ formulation decrease the inherent variability of EGCG and maintains a similar concentration range in all the volunteers subjected to the intake of EGCG-$Zn^{2+}$ composition.

TABLE 6

| Pharmacokinetics parameters EGCG-$Zn^{2+}$ complex | | |
|---|---|---|
| $AUC_{0\text{-}180\ min}$ | $T_{max}$ (min) | $C_{max}$ (ng/ml) |
| 15.33 ± 0.69 µg/mL/3 h | 60 | 109, 4 |

US PATENT DOCUMENTS

| | | |
|---|---|---|
| Hensley et al. (2011) | US20110257258A1 | Influenza |
| Kester et al (2008) | US7419693B2 | |
| Morré et al. (2009) | US007491413B2 | HIV-1, Rhinovirus |
| Pereira et al (2017) | US20170165297A1 | |
| Polansky et al (2011) | US20110052727A1 | Influenza |
| Rosenbloom (2008) | US007405046B2 | Rhinovirus |
| Seron et al. (2014) | US20140088184A1 | Hepatitis C |
| Shimamura et al (1992) | US005137922A | Influenza |
| Vajdy et al (2016) | US20160158350A1 | |

FOREIGN PATENT DOCUMENTS

| | | |
|---|---|---|
| Berg (2008) | CN100411617C | Broad spectrum |
| Berg (2008) | ES2298618T3 | |
| Chang et al. (2013) | CN105687226A | Coronavirus |
| Chang et al (2016) | CN105560268A | Influenza |
| Chang et al (2017) | WO2017124831A1 | Broad spectrum |
| Chang et al (2018) | CN105535012A | Broad spectrum |
| Furukawa et al (2015) | EP1655292B1 | BCV, coronavirus |
| Hou Wei et al (2015) | CN105030757A | Syncytial virus |
| Ichitani et al (2015) | JP2011126834A | Influenza |
| Katayama et al. (2005) | JP2005314316A | SARS |
| Kubo et al (2008) | JPWO2006100710A1 | SARS |
| Park Ki-duk et al (2008) | KR100792626B1 | Influenza |
| Pereira et al (2017) | CN104837369B | |
| Shau-Yi Liou et al (2005) | TW200533342A | SARS |
| Shimamura et al (1994) | EP0417385B1 | Influenza |
| Seihikohara et al (1998) | JP2727471B2 | Influenza |

-continued

| | | |
|---|---|---|
| Xu Donghui et al. (2005) | CN100435790C | |
| Yamamoto et al (2002) | EP1157693A1 | |
| Yoshiyuki et al (2015) | JP2015214501 | HSV, HIV |
| Yang Zhanqiu (2007) | CN1994294A | Broad spectrum |
| Yoshinaka et al (2018) | JP2018024610A | SARS |
| Zhong et al (2015) | JP5670201B2 | Influenza |

OTHER PUBLICATIONS

Alhafez M, Kheder F, Aljoubbeh M. Synthesis, characterization and antioxidant activity of EGCG complexes with copper and zinc ions, *Journal of Coordination Chemistry* 2019; 72:2337-2350.

Bozym R A, Thompson R B, Stoddard A K, Fierke C A. Measuring picomolar intracellular exchangeable zinc in PC-12 cells using a ratiometric fluorescence biosensor. *ACS Chem Biol.* 2006; 1(2): 103-111.

Báez-Santos Y M, St John S E, Mesecar A D. The SARS-coronavirus papain-like protease: structure, function and inhibition by designed antiviral compounds. *Antiviral Res.* 2015; 115:21-38.

Bojkova D, Klann K, Koch B, Widera M, Krause D, Ciesek S, Cinatl J, Munch C. Proteomics of SARS CoV-2-infected host cells reveals therapy targets. *Nature* 2020: 583(7816): 469-472

Callaway E, Cyranoski D, Mallapaty S, Stoye E, Tollefson J. The coronavirus pandemic in five powerful charts. *Nature.* 2020 Mar. 18.

Clergeaud G, Dabbagh-Bazarbachi H, Ortiz M, Fernández-Larrea J B, O'Sullivan C K. A simple liposome assay for the screening of zinc ionophore activity of polyphenols. *Food Chem.* 2016; 197(Pt A):916-923.

Colpitts, C. C.; Schang, L. M. A small molecule inhibits virion attachment to heparan sulfate- or sialic acid-containing glycans. *J Virol.* 2014, 88, 7806-7817

Colvin R A, Bush A I, Volitakis I, et al. Insights into $Zn^{2+}$ homeostasis in neurons from experimental and modeling studies. *Am J Physiol Cell Physiol.* 2008; 294(3):C726-C742. doi:10.1152/ajpcell.00541.2007

Chaturvedi U, Shrivastava R, Upreti R. Viral infections and trace elements: A complex interaction. *Current Science* 2004; 87(11):1536-1554.

Dabbagh-Bazarbachi H, Clergeaud G, Quesada I M, Ortiz M, O'Sullivan C K, Fernández-Larrea J B. Zinc ionophore activity of quercetin and epigallocatechin-gallate: from Hepa 1-6 cells to a liposome model. *J Agric Food Chem.* 2014; 62(32):8085-8093

De Oliveira, A.; Adams, S. D.; Lee, L. H.; Murray, S. R.; Hsu, S. D.; Hammond, J. R.; Dickinson, D.; Chen, P.; Chu, T. C. Inhibition of herpes simplex virus type 1 with the modified green tea polyphenol palmitoyl-epigallocatechin gallate. *Food Chem. Toxicol.* 2013; 52:207-215.

Eby G A, Davis D R, Halcomb W W. Reduction in duration of common colds by zinc gluconate lozenges in a double-blind study. *Antimicrob Agents Chemother.* 1984; 25(1): 20-24.

Feng S, Shen C, Xia N, Song W, Fan M, Cowling B J. Rational use of face masks in the COVID-19 pandemic. *Lancet Respir Med.* 2020 Mar. 20.

Furuta, T.; Hirooka, Y.; Abe, A.; Sugata, Y.; Ueda, M.; Murakami, K.; Suzuki, T.; Tanaka, K.; Kan, T. Concise synthesis of dideoxy-epigallocatechin gallate (DO-EGCG) and evaluation of its anti-influenza virus activity. *Bioorg. Med. Chem. Lett.* 2007; 17: 3095-3098

Henss L, Auste A, Schtirmann C, Schmidt C, von Rhein C, MUhlebach M D, Schnierle B S. The green tea catechin epigallocatechin gallate inhibits SARS-CoV-2 infection. *J Gen Virol.* 2021 April; 102(4).

Hurst et al Epigallocatechin-3-Gallate (EGCG) Inhibits SARS-CoV-2 Infection in Primate Epithelial Cells *Microbiol Infect Dis.* 2021 April; 5(2): 1-6.

Hong S, Seo S H, Woo S J, Kwon Y, Song M, Ha N C. Epigallocatechin Gallate Inhibits the Uridylate-Specific Endoribonuclease Nsp15 and Efficiently Neutralizes the SARS-CoV-2 Strain. *J Agric Food Chem.* 2021 Jun. 2; 69(21):5948-5954.

Huang, H. C.; Tao, M. H.; Hung, T. M.; Chen, J. C.; Lin, Z. J.; Huang, C. (−)-Epigallocatechin-3-gallate inhibits entry of hepatitis B virus into hepatocytes. *Antivir. Res.* 2014; 111:100-111.

Han Y S, Chang G G, Juo C G, et al. Papain-like protease 2 (PLP2) from severe acute respiratory syndrome coronavirus (SARS-CoV): expression, purification, characterization, and inhibition. *Biochemistry.* 2005; 44(30): 10349-10359.

Hsu J T, Kuo C J, Hsieh H P, et al. Evaluation of metal-conjugated compounds as inhibitors of 3CL protease of SARS-CoV. *FEBS Lett.* 2004; 574(1-3):116-120.

Isaacs, C. E.; Wen, G. Y.; Xu, W. M.; Jia, J. H.; Rohan, L.; Corbo, C.; Di Maggio, V.; Jenkins, E. C., Jr.; Hillier, S. Epigallocatechin gallate inactivates clinical isolates of herpes simplex virus. *Antimicrob. Agents Chemother.* 2008; 52:962-970.

Ishii T, Mori T, Tanaka T, Mizuno D, Yamaji R, Kumazawa S, Nakayama T, Akagawa M. Covalent modification of proteins by green tea polyphenol (−)-epigallocatechin-3-gallate through autoxidation. *Free Radic Biol Med.* 2008 Nov. 15; 45(10):1384-94.

Kaihatsu K, Yamabe M, Ebara Y. Antiviral Mechanism of Action of Epigallocatechin-3-O-gallate and Its Fatty Acid Esters. *Molecules.* 2018 Sep. 27; 23(10):2475

Kopecky-Bromberg S A, Martinez-Sobrido L, Frieman M, Baric R A, Palese P. Severe acute respiratory syndrome coronavirus open reading frame (ORF) 3b, ORF 6, and nucleocapsid proteins function as interferon antagonists. *J Virol.* 2007; 81(2):548-557

Krenn B M, Gaudernak E, Holzer B, Lanke K, Van Kuppeveld F J M, et al. Antiviral Activity of the Zinc Ionophores Pyrithione and Hinokitiol against Picornavirus Infections. *J Virol* 2009; 83: 58-64.

Ling J X, Wei F, Li N, et al. Amelioration of influenza virus-induced reactive oxygen species formation by epigallocatechin gallate derived from green tea. *Acta Pharmacol Sin.* 2012; 33(12): 1533-1541.

Lotfinejad N, Peters A, Pittet D. Hand hygiene and the novel coronavirus pandemic: The role of healthcare workers. *J Hosp Infect.* 2020 Mar. 19

Matsumoto M, Mukai T, Furukawa S, Ohori H. Inhibitory effects of epigallocatechin gallato on the propagation of bovine coronavirus in Madin-Darby bovine kidney cells. *Animal Science Journal* 2005; 76(5): 507-512, 75.

Maxfield L, Crane J S. Zinc Deficiency. [Updated 2019 Nov. 14]. In: StatPearls [Internet]. Treasure Island (FL): StatPearls Publishing; 2020 January-. Available from: https://www.ncbi.nlm.nih.gov/books/NBK493231/Nakayama M, Suzuki K, Toda M, Okubo S, Hara Y, Shima-mura T. 1993. Inhibition of the infectivity of influenza virus by tea polyphenols. *Antiviral Research* 21, 289-299.

Nguyen T T, Woo H J, Kang H K, et al. Flavonoid-mediated inhibition of SARS coronavirus 3C-like protease expressed in *Pichia pastoris. Biotechnol Lett.* 2012; 34:831-8.

Niemeyer D, Mosbauer K, Klein E M, et al. The papain-like protease determines a virulence trait that varies among members of the SARS-coronavirus species. *PLoS Pathog.* 2018; 14(9): e1007296.

Prasad A S. Zinc: role in immunity, oxidative stress and chronic inflammation. *Curr Opin Clin Nutr Metab Care.* 2009; 12(6): 646-652.

Quesada I M, Bustos M, Blay M, et al. Dietary catechins and procyanidins modulate zinc homeostasis in human HepG2 cells. *J Nutr Biochem.* 2011; 22(2):153-163.

Roh Ch. A facile inhibitor screening of SARS coronavirus N protein using nanoparticle-based RNA oligonucleotide. *Int J Nanomed* 2012; 7:2173-2179.

Samutprasert P, Chiablaem K, Teeraseranee C, et al. Epigallocatechin gallate-zinc oxide co-crystalline nanoparticles as an anticancer drug that is non-toxic to normal cells. *RSC Adv* 2018; 8:7369-7376.

Shiha G, Soliman R, Elbasiony M, Darwish N H E, Mousa S A. Addition of Epigallocatechin Gallate 400 mg to Sofosbuvir 400 mg+Daclatisvir 60 mg With or Without Ribavirin in Treatment of Patients with Chronic Hepatitis C Improves the Safety Profile: A Pilot Study. *Sci Rep.* 2019; 9(1):13593.

Skalny A V, Rink L, Ajsuvakova O P, et al. Zinc and respiratory tract infections: Perspectives for COVID-19 (Review) [published online ahead of print, 2020 Apr. 14]. *Int J Mol Med.* 2020; 46(1): 17-26. doi:10.3892/ijmm.2020.4575

Steinmann J, Buer J, Pietschmann T, Steinmann E. Anti-infective properties of epigallocatechin-3-gallate (EGCG), a component of green tea. *Br J Pharmacol.* 2013 March; 168(5): 1059-73.

Suara R O, Crowe J E J (2004) Effect of zinc salts on respiratory syncytial virus replication. *Antimicrob Agents Chemother* 48: 783-790.

Surjit M, Lal S K. The SARS-CoV nucleocapsid protein: a protein with multifarious activities. *Infect Genet Evol.* 2008; 8(4): 397-405.

te Velthuis A J, van den Worm S H, Sims A C, Baric R S, Snijder E J, van Hemert M J. Zn(2+) inhibits coronavirus and arterivirus RNA polymerase activity in vitro and zinc ionophores block the replication of these viruses in cell culture. *PLoS Pathog.* 2010; 6(11): e1001176.

Thambiayya K, Kaynar A M, St Croix C M, Pitt B R. Functional role of intracellular labile zinc in pulmonary endothelium. *Pulm Circ.* 2012; 2(4):443-451.

Uchide N, Ohyama K, Bessho T, Yuan B, Yamakawa T (2002) Effect of antioxidants on apoptosis induced by influenza virus infection: inhibition of viral gene replication and transcription with pyrrolidine dithiocarbamate. *Antiviral Res* 56: 207-217.

Vabret N, Britton G J, Gruber C, et al. Immunology of COVID-19: Current State of the Science [published online ahead of print, 2020 May 6]. *Immunity.* 2020; S1074-7613(20)30183-7.

Wu C, Liu Y, Yang Y, et al. Analysis of therapeutic targets for SARS-CoV-2 and discovery of potential drugs by computational methods. *Acta Pharm Sin B.* 2020; 10(5): 766-788.

Xu J et al A Review of the Antiviral Role of Green Tea Catechins. *Molecules* 2017 Aug. 12; 22(8). pii: E1337.

Yang J G, Yu H N, Sun S L, et al. Epigallocatechin-3-gallate affects the growth of LNCaP cells via membrane fluidity and distribution of cellular zinc. *J Zhejiang Univ Sci B.* 2009; 10(6):411-421.

Yen M Y, Schwartz J, Chen S Y, King C C, Yang G Y, Hsueh P R. Interrupting COVID-19 transmission by implementing enhanced traffic control bundling: Implications for global prevention and control efforts. *Microbiol Immunol Infect.* 2020; 53(3):377-380.

Zhang L, Lin D, Sun X, et al. Crystal structure of SARS-CoV-2 main protease provides a basis for design of improved α-ketoamide inhibitors. *Science.* 2020; 368 (6489):409-412

Zhang H; Zhao Y. Preparation, characterization and evaluation of tea polyphenol—Zn complex loaded β-chitosan nanoparticles. *Food Hydrocolloids* 2015; 48:260-273.

Zhong, L.; Hu, J.; Shu, W.; Gao, B.; Xiong, S. Epigallocatechin-3-gallate opposes HBV-induced incomplete autophagy by enhancing lysosomal acidification, which is unfavorable for HBV replication. *Cell Death Dis.* 2015, 6, e1770.

The invention claimed is:

1. A method for treating a patient against enveloped viruses infectious diseases caused by at least one virus, comprising the step of providing to the patient in need thereof a formulation containing EGCG-$Zn^{2+}$ complexes represented by the formulae:

A

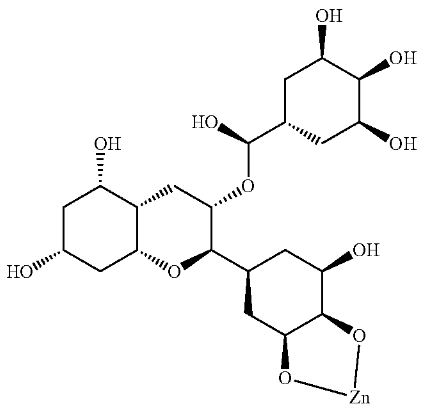

1:1

-continued

B

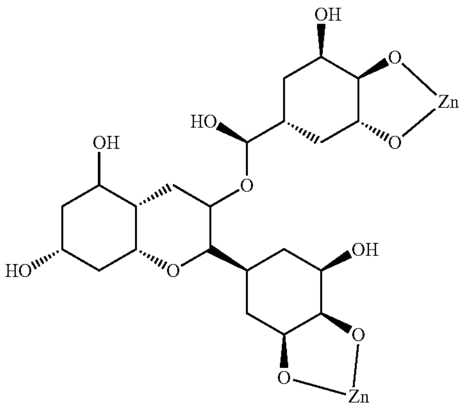

1:2

C

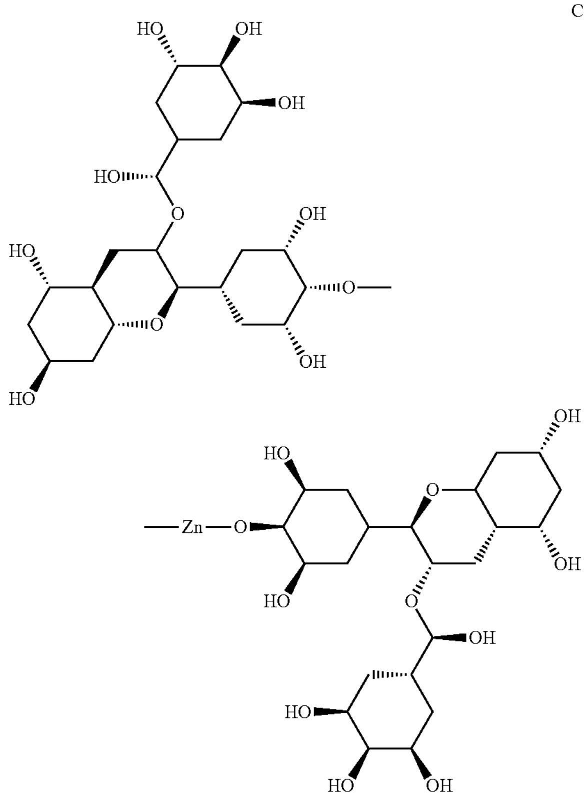

2:1 wherein the EGCG-$Zn^{2+}$ complexes conformations were modeled in proportions EGCG-$Zn^{2+}$ of 1:1, 1:2 and 2:1, the at least one enveloped virus infection is treatable with the EGCG-$Zn^{2+}$ complexes based on high suppressive synergistic activity and low toxicity associated with the EGCG-$Zn^{2+}$, and the at least one enveloped virus infection comprising at least SARS-CoV-2.

2. The method of claim 1, comprising the step of providing at least once a day to a human or animal in need thereof, a formulation containing a combination of at least 10 mg up to 1000 mg of EGCG and at least 1 mg up to 30 mg of Zn in the form of EGCG-$Zn^{2+}$ complexes, during a time at least between 1-30 days, when the individual is considered healthy, wherein the antiviral effect and efficacy of EGCG and/or Zn is enhanced.

3. The method of claim 1, wherein the infectious disease is caused in humans by an enveloped virus and is treated by providing at least once a day to an individual in need thereof, a formulation containing a combination of at least 10 mg up to 1000 mg of EGCG and at least 1 mg up to 30 mg of Zn in the form of EGCG-$Zn^{2+}$ complexes, during a time at least between 1-30 days when the individual is considered to be out of risk of infection or healthy.

4. The method of claim 1, wherein the bioavailability of EGCG for clinical use is improved by providing at least once a day to a human or animal in need thereof, a formulation containing a combination of at least 10 mg up to 1000 mg of EGCG and at least 1 mg up to 30 mg of Zn in the form of EGCG-$Zn^{2+}$ complexes, during a time at least between 1-30 days.

5. The method of claim 1, wherein immunologic complications from an infectious disease caused in humans by an enveloped virus is treated by providing at least once a day to an individual in need thereof, a formulation containing a combination of at least 10 mg up to 1000 mg of EGCG and at least 1 mg up to 30 mg of Zn in the form of EGCG-$Zn^{2+}$ complexes, during a time at least between 1-30 days when the individual is considered to be out of risk of immunologic complications or healthy.

6. The method of claim 1, wherein toxicity is decreased, tolerability is increased and safety issues are minimized with the clinical use of EGCG when providing at least once a day to an individual in need thereof, a formulation containing a combination of at least 10 mg up to 1000 mg of EGCG and at least 1 mg up to 30 mg of Zn in the form of EGCG-$Zn^{2+}$ complexes, during a time at least between 1-30 days.

7. The method of claim 1, wherein the formulation is administered in sufficient quantity for the prophylaxis of a disease caused in humans by emergent viruses.

8. The method of claim 1, wherein the formulation is administered in sufficient quantity for the early treatment of a disease caused in humans by enveloped viruses.

9. The method of claim 1, wherein the formulation is administered in sufficient quantity to alleviate and shorten symptoms caused in humans by enveloped viruses.

10. The method of claim 1, wherein the formulation is administered as a complement or adjuvant to standard therapies used for the treatment of diseases caused in humans by enveloped viruses.

11. The method of claim 1, wherein the formulation is administered as inhibitor of the viral translation in experiments involving enveloped viruses.

12. The method of claim 1, wherein the formulation is administered as inhibitor of the viral adsorption in experiments involving enveloped viruses.

13. The method of claim 1, wherein the formulation is administered as inhibitor of the viral absorption in experiments involving enveloped viruses.

14. The method of claim 1, wherein the formulation is administered as inhibitor of the viral replication in experiments involving enveloped viruses.

15. The method of claim 1, wherein the formulation is administered as inhibitor of the Papain-Like-Protein (PLP) of SARS-CoVs.

16. The method of claim 1, wherein the formulation is administered as inhibitor of the main protease 3CLpro of SARS-CoVs.

17. The method of claim 1, wherein the formulation is administered as inhibitor of the RNA dependent RNA polymerase (RdRp) of SARS-CoVs.

18. The method of claim 1, wherein the formulation is administered as inhibitor of the Spike Protein(S) of SARS-CoVs.

19. The method of claim 1, wherein the formulation is administered as inhibitor of the NSP15 of SARS-CoV-2 by interfering or blocking its active domain.

20. The method of claim 1, wherein the formulation is administered as an immunomodulatory medication to treat an infection with an emergent enveloped virus.

21. The method of claim 1, wherein the formulation is administered as inhibitor of the domain RBD-ACE2 by interfering or blocking the viral adsorption of SARS-CoV-2.

22. The method of claim 1, wherein the formulation is administered orally, intravenously, intramuscularly, endonasal, and subcutaneously for the treatment of a disease caused in humans by enveloped viruses.

23. The method of claim 1, wherein the formulation is administered as aerosol or nebulization for the treatment of a disease caused in humans by enveloped viruses.

24. The method of claim 1, wherein the formulation is administered for inhibiting the Papain-Like-Protein (PLP) of SARS-CoVs by interacting with the amino acids ASN-109A, GLY-160A, GLU-161A, LEU-162A, GLN-269A, GLN-160B, GLU-161B, LEU-162B, GLN-269B, HIS-89C, ASP-108C, ASN-109C, VAL-159C, GLY-160C, and GLN-269C.

25. The method of claim 1, wherein the formulation is administered for inhibiting the main protease 3CLpro of SARS-CoVs by interacting with the amino acids THR-26, LEU-27, HIS-41, MET-49, TYR-54, PHE-140, LEU-141, ASN-142, CYS-145, HIS-164, MET-165, GLU-166, ASP-187, ARG-188, and GLN-189.

26. The method of claim 1, wherein the formulation is administered for inhibiting the RNA dependent RNA polymerase (RpRd) of SARS-CoVs by interacting with the amino acids LEU-270, PRO-323, THR-324, PHE-326, PHE-396, and VAL-675.

27. The method of claim 1, wherein the formulation is administered for inhibiting the Spike Protein(S) of SARS-CoVs by interacting with the amino acids LEU-546A, THR-547A, ASP-568A, THR-572A, THR-573A, PRO-589A, MET-740B, TYR-741B, ILE-742B, CYS-743B, GLY-744B, ASP-745B, PHE-855B, ASN-856B, VAL-976B, ASN-978B, and ARG-1000B.

28. The method of claim 1, wherein the formulation is administered for inhibiting the NSP15 of SARS-CoV-2 by interfering or blocking its active domain made up of amino acids HIS-235, GLY-248, HIS-250, LYS-290, CYS-291, VAL-292, SER-294, TRP-333, THR-341, TYR-343, PRO-344, LYS-345, and LEU-346.

29. The method of claim 1, wherein the formulation is administered for inhibiting the NSP15 of SARS-CoV-2 by interfering or blocking the amino acids LYS-71, LYS-90, THR-167, THR-196, GLN-197, SER-198, ARG-199, ASN-200, LEU-252, ASP-273, SER-274, THR-275, LYS-277, TYR-279, VAL-295, ILE-296, and ASP-297.

30. The method of claim 1, wherein the formulation is administered for inhibiting the domain RBD-ACE2 by interacting with the amino acids ILE-291, MET-366, ASP-367, LEU-370, THR-371, HIS-374, GLU-406, SER-409, LEU-410, PHE-438, GLN-442, and ILE-446.

* * * * *